(12) United States Patent
Dalal

(10) Patent No.: US 8,470,440 B2
(45) Date of Patent: Jun. 25, 2013

(54) REGENERATIVE NON-TACKY ADHESIVE FASTENING SYSTEM FOR USE IN CONSUMER PRODUCTS

(75) Inventor: Urmish Dalal, Milford, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1996 days.

(21) Appl. No.: 11/512,446

(22) Filed: Aug. 30, 2006

(65) Prior Publication Data

US 2008/0058753 A1    Mar. 6, 2008

(51) Int. Cl.
*B32B 7/12* (2006.01)
*B32B 15/04* (2006.01)

(52) U.S. Cl.
USPC .......................................... 428/343; 428/354

(58) Field of Classification Search
USPC .................................. 428/343, 354
See application file for complete search history.

(56) References Cited

U.S. PATENT DOCUMENTS

| | | |
|---|---|---|
| 3,574,864 A | 4/1971 | Bradley |
| 3,848,594 A | 11/1974 | Buell |
| 3,860,003 A | 1/1975 | Buell |
| 4,515,595 A | 5/1985 | Kievit et al. |
| 4,610,678 A | 9/1986 | Weisman et al. |
| 4,662,875 A | 5/1987 | Hirotsu et al. |
| 4,673,402 A | 6/1987 | Weisman et al. |
| 4,695,278 A | 9/1987 | Lawson |
| 4,710,189 A | 12/1987 | Lash |
| 4,795,454 A | 1/1989 | Dragoo |
| 3,860,003 B1 | 4/1989 | Buell |
| 4,834,735 A | 5/1989 | Alemany et al. |
| 4,846,815 A | 7/1989 | Scripps |
| 4,888,231 A | 12/1989 | Angstadt |
| 4,892,536 A | 1/1990 | Desmarais et al. |
| 4,894,060 A | 1/1990 | Nestegard |
| 3,860,003 B2 | 6/1990 | Buell |
| 4,946,527 A | 8/1990 | Battrell |

(Continued)

FOREIGN PATENT DOCUMENTS

| | | |
|---|---|---|
| WO | WO-99/32005 A1 | 7/1999 |
| WO | WO-2005/077313 A1 | 8/2005 |
| WO | WO 2005/122987 A | 12/2005 |
| WO | WO 2005122987 * | 12/2005 |

OTHER PUBLICATIONS

International Search Report.

(Continued)

*Primary Examiner* — Victor Chang
(74) *Attorney, Agent, or Firm* — Amy M. Foust; Eric Addington; Abbey A. Lopez

(57) ABSTRACT

A non-tacky adhesive fastening system may have a first configuration and a second configuration. The non-tacky adhesive fastening system comprises an engaging member and a receiving member. In the first configuration, the engaging member comprises a first non-tacky member and the receiving member comprises an intermediate non-tacky member and a second non-tacky member. The intermediate non-tacky member is refastenably joined to the second non-tacky member. In the second configuration, the non-tacky adhesive fastening system comprises the engaging member having the first non-tacky member and the intermediate non-tacky member and the receiving member comprises the second non-tacky member. The second configuration is formed upon fastening the engaging surface of the first non-tacky member to the primary surface of the intermediate non-tacky member and separating the engaging member from the receiving member.

22 Claims, 9 Drawing Sheets

U.S. PATENT DOCUMENTS

| | | |
|---|---|---|
| 4,990,147 A | 2/1991 | Freeland |
| 5,037,416 A | 8/1991 | Allen et al. |
| 5,050,742 A | 9/1991 | Muckenfuhs |
| 5,054,619 A | 10/1991 | Muckenfuhs |
| 5,137,537 A | 8/1992 | Herron et al. |
| 5,147,345 A | 9/1992 | Young et al. |
| 5,151,092 A | 9/1992 | Buell et al. |
| 5,196,266 A | 3/1993 | Lu et al. |
| 5,221,274 A | 6/1993 | Buell et al. |
| 5,260,345 A | 11/1993 | Desmarais et al. |
| 5,269,775 A | 12/1993 | Freeland et al. |
| 5,342,338 A | 8/1994 | Roe |
| 5,387,207 A | 2/1995 | Dyer et al. |
| 5,397,316 A | 3/1995 | Lavon et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| 5,643,588 A | 7/1997 | Roe et al. |
| 5,669,897 A | 9/1997 | Lavon et al. |
| 5,865,823 A | 2/1999 | Curro |
| 5,899,895 A | 5/1999 | Robles et al. |
| 5,908,695 A * | 6/1999 | Kobe et al. .................... 428/354 |
| 5,934,470 A | 8/1999 | Bauer et al. |
| 6,004,306 A | 12/1999 | Robles et al. |
| 6,004,308 A | 12/1999 | Haddock |
| 6,013,589 A | 1/2000 | Desmarais et al. |
| 6,107,537 A | 8/2000 | Elder et al. |
| 6,120,487 A | 9/2000 | Ashton |
| 6,156,424 A | 12/2000 | Taylor |
| 6,159,596 A | 12/2000 | Calhoun et al. |
| 6,432,098 B1 | 8/2002 | Kline et al. |
| 6,764,475 B1 | 7/2004 | Olson |
| 2004/0162536 A1 | 8/2004 | Becker et al. |
| 2004/0167486 A1 | 8/2004 | Busam et al. |
| 2004/0180197 A1 | 9/2004 | Everaerts et al. |
| 2005/0031233 A1 | 2/2005 | Varanese et al. |
| 2005/0177127 A1 | 8/2005 | Ashton et al. |
| 2005/0277905 A1 * | 12/2005 | Pedersen et al. .............. 604/389 |
| 2007/0156111 A1 | 7/2007 | Dalal et al. |

OTHER PUBLICATIONS

International Search Report dated Apr. 29, 2008, 12 pages, PCT/ISA/237.

International Search Report dated Jul. 28, 2008, 6 pages, PCT/ISA/210.

International Search Report, PCT/ISA/210 dated Apr. 29, 2008.

* cited by examiner

REGENERATIVE NON-TACKY ADHESIVE FASTENING SYSTEM FOR USE IN CONSUMER PRODUCTS

FIELD OF THE INVENTION

The present invention relates to a non-tacky adhesive fastening system having a regenerative surface. The non-tacky adhesive fastening system may be incorporated in consumer goods such as absorbent articles or reclosable bags.

BACKGROUND OF THE INVENTION

Fastening systems are widely used in a variety of applications where fastening of components is required. Certain fastening systems are refastenable in that they are capable of multiple openings and closures. Items such as diapers and containers storing foodstuff or other consumer goods are commonly equipped with a fastening system and, typically, a refastenable fastening system. Such fastening systems may include an adhesive fastening system. However, adhesive fastening systems have drawbacks.

One such drawback of an adhesive fastening system includes the use of a traditional adhesive that sticks to surfaces indiscriminately. Such indiscriminate adhesive fastening systems are not ideal for use in consumer products such as diapers where inadvertent adhesion of the fastener to skin, hair, or clothing is undesirable. For example, consumers generally disfavor adhesive fastening systems with components that can adhere to skin. Such systems may be difficult to use and may cause irritation if attached to skin or hair (e.g., a baby may experience discomfort if an adhesive tape is removed from the baby's skin).

Another drawback of adhesive fastening systems is that the system may exhibit poor contamination resistance. An adhesive fastening system may become contaminated with foreign matter which degrades the fastening strength of the system. For example, fastening systems used in diapers often become contaminated with baby care products (e.g., baby powder, diaper ointment, baby oil, etc.) and by dirt and oils from the caregiver's hands. Typically, a fastening system will be exposed to some degree of contamination upon first use and with subsequent refastening events (i.e., separating and reengaging of a fastening system). These contaminants may degrade the fastening strength of the system. The result is that the fastening system may be unable to withstand the forces applied to it during use. For example, a diaper's fastening system may be unable to withstand the forces applied to it during wear such as, for example, the forces exerted by the movement of the wearer. This may result in the diaper inadvertently opening and leaking during wear.

Accordingly, a need exists for an adhesive fastening system that does not stick indiscriminately to surfaces and, particularly, does not appreciably stick to skin (i.e., non-tacky). Furthermore, a need exists for this non-tacky adhesive fastening system to exhibit sufficient contamination resistance to allow the fastening system to be refastenable.

SUMMARY OF THE INVENTION

In light of the problems with current fastening systems, the present invention relates to a non-tacky adhesive fastening system having a first configuration and a second configuration. In the first configuration, the non-tacky adhesive fastening system comprises an engaging member and a receiving member. The engaging member comprises a first non-tacky member, which has an engaging surface and a fixed surface. The receiving member comprises an intermediate non-tacky member, which has a primary surface and a secondary surface, and a second non-tacky member, which has a regenerative surface and a fixed surface. The secondary surface of the intermediate non-tacky member is refastenably joined to the regenerative surface of the second non-tacky member. The engaging surface of the first non-tacky member is remote from the primary surface of the intermediate non-tacky member. In the second configuration, the non-tacky adhesive fastening system comprises the engaging member having the first non-tacky member and the intermediate non-tacky member; wherein the primary surface of the intermediate non-tacky member is joined to the engaging surface of the first non-tacky member. In the second configuration, the receiving member comprises the second non-tacky member. The second configuration is formed upon fastening the engaging surface of the first non-tacky member to the primary surface of the intermediate non-tacky member and separating the engaging member from the receiving member.

The present invention further relates to a non-tacky adhesive fastening system comprising an engaging member and a receiving member. The engaging member comprises a first non-tacky member, which has an engaging surface and a fixed surface. The receiving member comprises an intermediate non-tacky member, which has a primary surface and a secondary surface, and a second non-tacky member, which has a regenerative surface and a fixed surface. The secondary surface of the intermediate non-tacky member is refastenably joined to the regenerative surface of the second non-tacky member. Upon fastening the engaging surface of the first non-tacky member and the primary surface of the intermediate non-tacky member, the engaging surface of the first non-tacky member and the primary surface of the intermediate non-tacky member exhibit a T-peel force greater than the T-peel force exhibited by the secondary surface of the intermediate non-tacky member and the regenerative surface of the second non-tacky member.

The present invention further relates to commercial goods including non-tacky adhesive fastening systems. Such commercial goods include, but are not limited to, absorbent articles and recloseable bags.

BRIEF DESCRIPTION OF THE DRAWINGS

In the accompanying drawing, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

DETAILED DESCRIPTION OF THE INVENTION

Figure 1A:
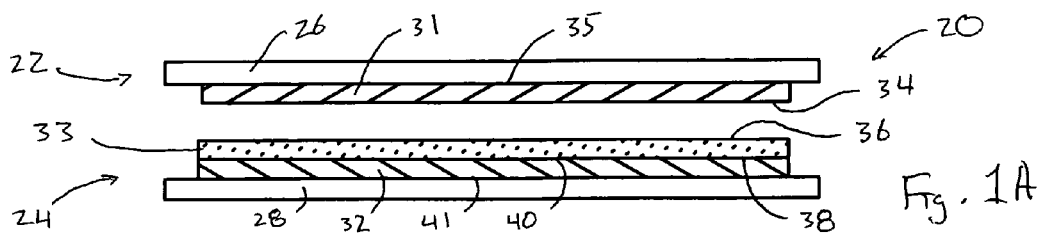
FIGS. 1A-E illustrate various configurations of an exemplary non-tacky adhesive fastening system having a regenerative surface.

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like. Absorbent articles may be disposable or may have portions that may be restored or renewed.

"Pant" refers to an absorbent article having a pre-formed waist opening and leg openings. A pant may be placed in position on the wearer by inserting the wearer's legs into the leg openings and sliding the pant into position about a wearer's lower torso. In contrast, an article may be provided in an "open" configuration (i.e., the fastening system is not pre-engaged and the article does not have a continuous waist and/or a pair of leg openings) where the consumer must engage the fastening system to form a continuous waist and enable the article to encircle the waist and legs of a wearer. A pant may include openable seams to aid donning and/or removal. Additionally, absorbent articles may be constructed with refastenable features allowing the article to have both a pant-like configuration and one or more configurations which not pant-like (i.e., traditional taped diaper).

"Proximal" and "Distal" refer respectively to the location of an element relatively near to or far from the longitudinal or lateral centerline of a structure.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal"

"Lateral" refers to a direction running from a longitudinal edge to an opposing longitudinal edge of the article and generally at a right angle to the longitudinal direction. Directions within 45 degrees of the lateral direction are considered to be "lateral."

"Longitudinal Centerline" refers to a longitudinal line that can be drawn through the middle of an absorbent article. For most absorbent articles, the longitudinal centerline separates the article into two substantially symmetrical halves that will fall on the left and right halves of a wearer during wear.

"Lateral Centerline" refers to a lateral line drawn through the midpoint of the longitudinal centerline and perpendicular to the longitudinal centerline.

"Disposed" refers to an element being located in a particular place or position.

"Extendibility" and "extensible" mean that the width or length of the component in a relaxed state can be extended or increased.

"Elastic," "elastomer," and "elastomeric" refer to a material which generally is able to extend to a strain of at least 50% without breaking or rupturing, and is able to recover substantially to its original dimensions after the deforming force has been removed.

"Elastomeric material" is a material exhibiting elastic properties. Elastomeric materials may include elastomeric films, scrims, nonwovens, and other sheet-like structures.

"Outboard" and "inboard" refer respectively to the location of an element disposed relatively far from or near to the longitudinal centerline of the diaper with respect to a second element. For example, if element A is outboard of element B, then element A is farther from the longitudinal centerline than is element B.

"Joined" refers to configurations whereby an element is directly secured to another element by affixing the element directly to the other element and to configurations whereby an element is indirectly secured to another element by affixing the element to intermediate member(s) which in turn are affixed to the other element.

"Refastenable" and "refastenably" refer to the attachment of two or more elements of a fastening system or portions of elements of a fastening system together in a manner in which they can be separated and re-attached without substantial degradation of fastener performance or damage to surrounding components of the article which would impair the article's continued use. It will be appreciated that a refastenable component need not have an infinite life span, but it is sufficient that the components attached in a refastenable manner can be separated and re-attached successively several times over the typical use life span of the article. It will also be appreciated that the aggressiveness of actual fastening may be reduced significantly from fastening to refastening in absolute terms, but that such reduction is not "substantial degradation" of fastener performance if the resulting refastened strength is sufficient for the fastening system's purpose of use.

"Fasten" refers to the engagement of two or more elements of a fastening system or portions of elements of a fastening system.

"Refasten" refers to the reengagement of a two or more elements of a fastening system or portions of elements of a fastening system that where previously engaged and separated.

"Refastening event" refers to the separating and reengaging of an engaged fastening system.

"Dwell Time" refers to the time in which two or more elements of a fastening system are in a fastened configuration.

"Non-tacky" refers to a material that exhibits low surface adhesion to synthetic skin as measured by Probe Tack Test Method described below. Low surface adhesion is quantified as a measurement of less than 50 grams force (gf) according to the Probe Tack Test Method. In certain embodiments, low surface adhesion may be less than 40 gf; alternately, less than 30 gf; alternately, less than 20 gf; alternately, less than 10 gf; or alternately, less than 5 gf. Conversely, "tacky" refers to material that exhibits a surface adhesion to synthetic skin as measured by Probe Tack Test Method described below of greater than 50 grams force (gf) as measured by Probe Tack Test Method.

"Lock-up" refers to the condition wherein one material is joined to a second material such that the materials cannot be separated without some form of catastrophic failure that prohibits refastening.

"Minimal T-peel force" refers to the lesser T-peel force exhibited by a first non-tacky member and an intermediate non-tacky member or a second non-tacky member and the intermediate non-tacky member as measured according to the T-Peel Test Method provided below.

"Adhesive fastening system" refers to a fastening system utilizing a traditional adhesive, a selective adhesive, or a cohesive for adhesion. Adhesive fastening systems are distinguishable from "mechanical fastening systems," which are fastening systems relying on physical restraint or engagement of portions of the fastener for operation, and "magnetic field fastening systems", which rely on magnets. Examples of mechanical fasteners are hook and loops, hooks and hooks, Velcro™, buttons, snaps, tab and slot, zippers, and tongue and groove fasteners.

"Typical adhesive" and "traditional adhesive" are interchangeable and refer to a material which demonstrates adhesion when applied to another material generally (e.g. material is not specially selected). Traditional adhesive materials connect to other materials indiscriminately and may stick to a variety of materials. Traditional adhesives are tacky. Generally, typical adhesive materials used in disposable absorbent articles demonstrate adhesion either at certain temperatures (such as a hot melt adhesive) or under pressure (a pressure sensitive adhesive).

"Oriented" refers to a polymer material that has been strained during manufacture to substantially align the molecular chains. "Bi-oriented" refers to a material that has been strained during manufacture in two directions; generally, the two directions are orthogonal to each other.

"Cohesive" refers to a material that demonstrates surface interaction (in terms of connection of one surface to another) when applied to itself or to an analog of itself. A cohesive system may be designated as an A-A system, where cohesive material A will fasten or form a connection primarily to itself. Generally, such cohesives are substantially non-tacky (such as to skin or synthetic skin) at room temperature or while under moderate pressure (e.g., finger pinch pressure).

"Selective adhesive" refers to a material which demonstrates surface interaction (in terms of connection of one surface to another) when applied to a specially selected second material. An A-A' type selective adhesive system demonstrates surface interaction where material A will stick to material A', where A' is a material that is chemically similar to A. An A-B type selective adhesive system demonstrates surface interaction properties where material A will stick to different material B. However, it should be noted that A' may also be a cohesive. For example, in an A-A' type selective system, A may also attach to A, and A' may attach to A'. In another example, an A-B type selective adhesive system could also exist where a material A may attach to itself or to material B, but material B will not attach to itself. Materials A, A', and B may be non-tacky.

FIGS. 1A-E illustrates an exemplary non-tacky adhesive (NTA) fastening system 20 having a regenerative surface. The NTA fastening system 20 has a first configuration and a second configuration. The first configuration is generally the configuration of the NTA fastening system 20 upon manufacture and delivery to an end user. The second configuration is generally the configuration of the NTA fastening system 20 after an initial engagement and separation of the system 20 by the end user. The second configuration results in the exposure of surfaces that may be used for subsequent fastening wherein the exposed surfaces were not exposed in the first configuration.

FIG. 1A shows the NTA fastening system 20 in the first configuration such as may be provided to a user. The system 20 generally may comprise an engaging member 22, receiving member 24, and an intermediate non-tacky (NT) member 33. The engaging member 22 may comprise an engaging substrate 26 with a first non-tacky (NT) member 31 disposed thereon. The first NT member 31 includes an engaging surface 34 that may be attached to the receiving member 24 and a fixed surface 35 that may be joined to the engaging substrate 26. The receiving member 24 may have a receiving substrate 28 with second non-tacky (NT) member 32 disposed thereon. The second NT member 32 may have a fixed surface 41 that may be disposed on the receiving substrate 28. The second NT member 32 may have a regenerative surface 40. The intermediate NT member 33 may have a primary surface 36 and a secondary surface 38. In this first configuration, the secondary surface 38 may be disposed in a face-to-face relationship with the regenerative surface 40 of the second NT member 32. The intermediate NT member 33 may be continuously disposed on the second NT member 32 (as shown in FIG. 1A) or may be discontinuously disposed (e.g., stripes or dots of the intermediate NT member 33 on the second NT member 32). In this first configuration, the primary surface 36 of the intermediate NT member 33 is remote from the engaging surface 34 of the first NT member 31 but the two surfaces 34, 36 may be joined.

Figure 1B:
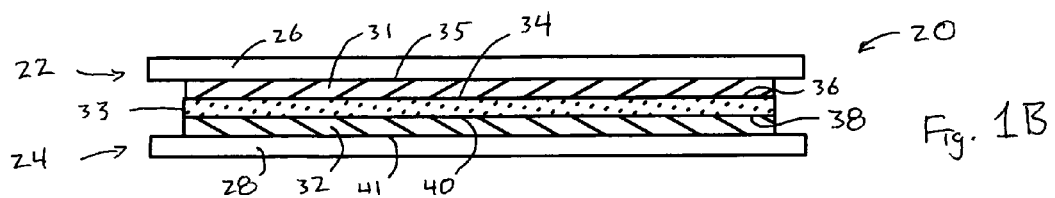

FIG. 1B shows the NTA fastening system 20 in a fastened configuration with the engaging surface 34 of the first NT member 31 joined in a face-to-face relationship with the primary surface 36 of the intermediate NT member 33. In this state, the engaging member 22 and the receiving member 24 are considered to be fastened (or engaged). The NTA fastening system 20 should be capable of maintaining this fastened configuration for a suitable length of time (e.g., dwell time). In other words, there should be no appreciable degradation of adhesion during the normal use time of the NTA fastening system 20. For example, if used in an absorbent article such as a diaper, the typical wear time of such articles may be between about 2 hours to about 12 hours. In certain embodiments, the NTA fastening system 20 may remain fastened for at least about 2 hours or at least about 6 hours before separating.

Figure 1C:
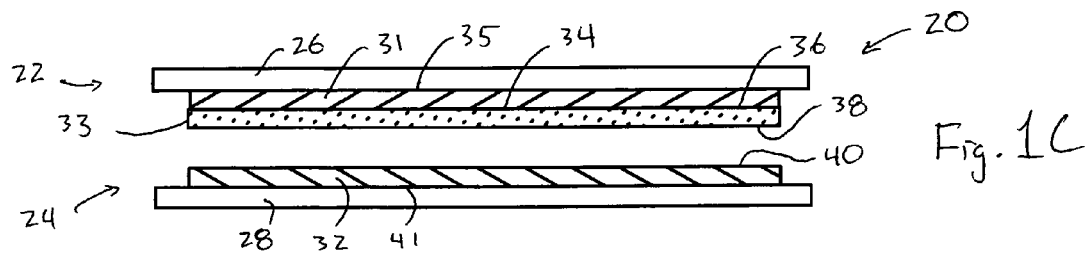

FIG. 1C illustrates the NTA fastening system 20 in a second configuration where the engaging member 22 is no longer joined to the receiving member 24. In this configuration, the intermediate NT member 33 is joined to the first NT member 31. The primary surface 36 of the intermediate NT member 33 is joined in a face-to-face relationship with the engaging surface 34 of the first NT member 31. The secondary surface 38 of the intermediate NT member 33 is now exposed and may be used for subsequent fastening. Likewise, the regenerative surface 40 the second NT member 32 is now exposed and may be used for subsequent fastening.

Figure 1D:
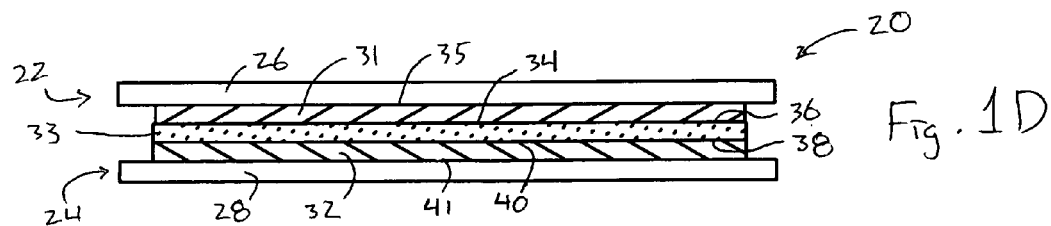

FIG. 1D illustrates the NTA fastening system 20 in a refastened configuration where the secondary surface 38 of the intermediate NT member 33 is joined in a face-to-face relationship with the regenerative surface 40 of the second NT member 32. In this state, the engaging member 22 and the receiving member 24 are considered to be refastened (or reengaged). The NTA fastening system 20 should be capable of maintaining this refastened configuration for a suitable length of time (i.e., dwell time). In other words, there should be no appreciable degradation of adhesion during the normal use time of the NTA fastening system 20 in the refastened state. For example, if used in an absorbent article such as a diaper, the typical wear time of such articles may be between about 2 hours to about 12 hours.

Figure 1E:
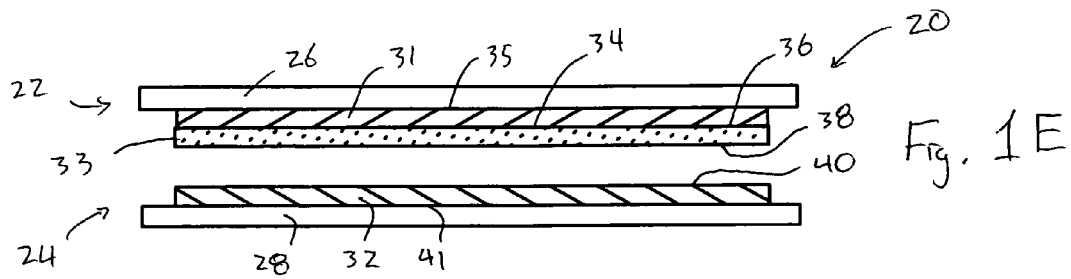

The NTA fastening system 20 may be separated yet again such that the engaging member 22 is no longer joined to the receiving member 24. FIG. 1E depicts that, upon separation, the NTA fastening system may be in an orientation substantially similar to the one shown in FIG. 1C (i.e., the second configuration). In this configuration, the secondary surface 38 of the intermediate NT member 33 is again exposed and may be used for subsequent fastening. Likewise, the regenerative surface 40 the second NT member 32 is again exposed and may be used for subsequent fastening. Additional refastening events (i.e., separating and reengaging of the NTA fastening system 20) may occur and the present invention is not limited in the particular number of refastening events that may occur for any of the embodiments presented.

In another suitable embodiment, as depicted in FIGS. 2A-E, the NTA fastening system 20 may be constructed without the need for an engaging substrate 26 (as shown in FIGS. 1A-E) or a receiving substrate 28 (as shown in FIGS. 1A-E). In the embodiment shown in FIG. 2A, the engaging member 22 initially comprises the first NT member 31 having an engaging surface 34. The receiving member 24 initially comprises the second NT member 32 having regenerative surface 40. The intermediate NT member 33 may have a primary surface 36 and a secondary surface 38. In this first configuration, the secondary surface 38 of the intermediate NT member 33 may be disposed in a face-to-face relationship with the regenerative surface 40 of the second NT member 32. In this first configuration, the primary surface 36 of the intermediate NT member 33 is remote from the engaging surface 34 of the first NT member 31 but the two surfaces 34, 36 may be joined. In select variants of this embodiment, at least the first NT member 31 and the second NT member 32 exhibit sufficient tensile strength to inhibit substantial elongation (i.e., greater than 10% strain) at the forces necessary to achieve separation of the engaged NTA fastening system 20 or the minimal T-Peel force. In other words, the first NT member 31 and the second NT member 32 should be selected such that the engaged NTA fastening system 20 separates prior to substantial elongation of the first NT member 31 and the second NT member 32.

Figure 2A:
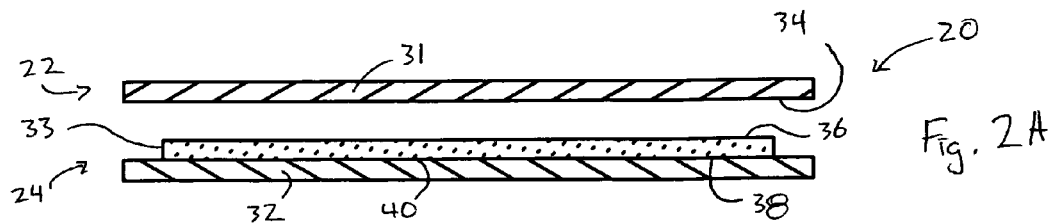
FIGS. 2A-E illustrate various configurations of another exemplary non-tacky adhesive fastening system having a regenerative surface.
Figure 2B:
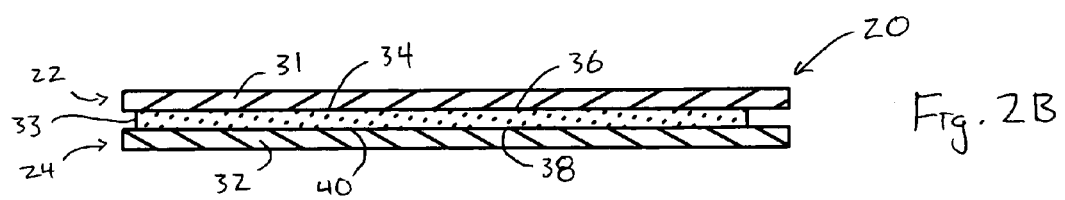
Figure 2C:
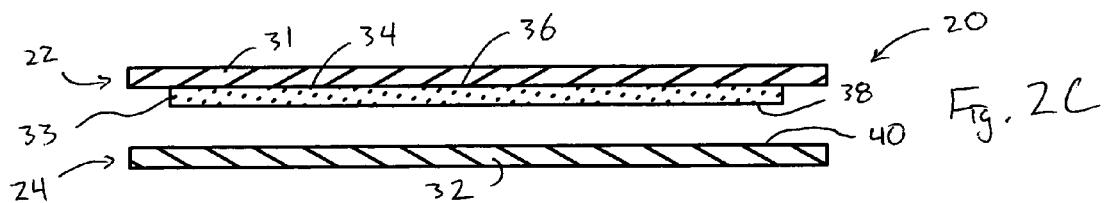
Figure 2D:
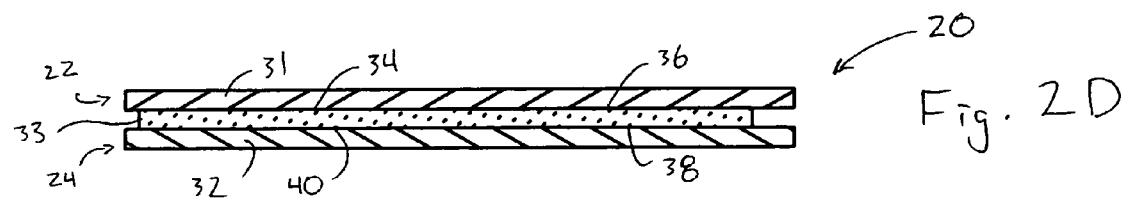
Figure 2E:
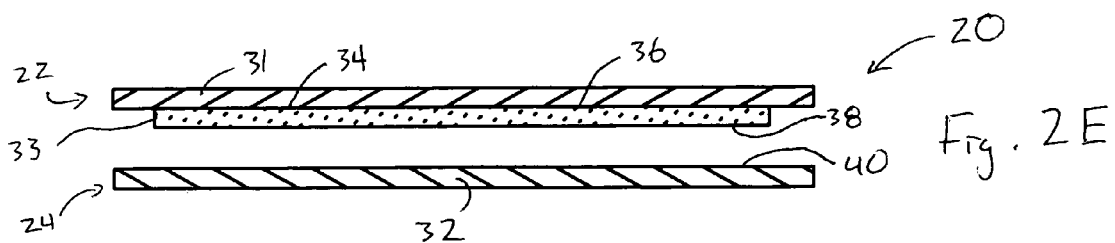

FIGS. 2B-E are substantially similar in operation to FIGS. 1B-E, respectively. FIG. 2B shows the NTA fastening system 20 in an engaged configuration with the engaging surface 34 of the first NT member 31 joined in a face-to-face relationship with the primary surface 36 of the second NT member 32. FIG. 2C illustrates the NTA fastening system 20 in the second such that the engaging member 22 is no longer joined to the receiving member 24. In this configuration, the intermediate NT member 33 is joined in the first NT member 31. The primary surface 36 of the intermediate NT member 33 is joined in a face-to-face relationship with the engaging surface 34 of the first NT member 31. The secondary surface 38 of the intermediate NT member 33 is now exposed and may be used for subsequent fastening. Likewise, the regenerative surface 40 of the second NT member 32 is now exposed and may be used for subsequent fastening. FIG. 2D illustrates the NTA fastening system 20 in a refastened configuration where the secondary surface 38 of the intermediate NT member 33 is joined in a face-to-face relationship with the regenerative surface 40 of the second NT member 32. FIG. 2E depicts that upon separation the NTA fastening system may be in an orientation substantially similar to the one shown in FIG. 2C. In this configuration, the secondary surface 38 of the intermediate NT member 33 and the regenerative surface 40 of the second NT member 32 are again exposed and may be used for subsequent fastening.

Generally, the engaging member 22 and the receiving member 24 may be any two items or portions of a single item that can be joined together by way of the NTA fastening system 20. In embodiments including an engaging substrate 26 and receiving substrate 28, the engaging substrate 26 and/or the receiving substrate 28 may comprise any number of suitable webs, materials, or objects. The engaging substrate 26 and receiving substrate 28 may be a sheet material wherein the dimensions on the largest planar face exceed, often by many orders of magnitude, the caliper or thickness of the sheet. Such sheet material may be polymeric films, metallic films, nonwoven materials, woven materials, paper, cardboard, paperboard, and combinations thereof (e.g., composites and laminates). In certain embodiments, the engaging substrate 26 and/or receiving substrate 28 may be constructed from a material with sufficient tensile strength that it can be processed and handled at commercially feasible speeds. In certain embodiments, the engaging substrate 26 may be constructed from the same material as the first NT member 31. In certain embodiments, the receiving substrate 28 may be constructed from the same material as the second NT member 32.

In certain embodiments, the engaging substrate 26 and/or receiving substrate 28 may exhibit sufficient tensile strength to inhibit substantial elongation (i.e., greater than 10% strain) at a minimal T-peel force necessary to achieve separation of the engaged NTA fastening system 20. In other words, the engaging substrate 26 and/or the receiving substrate 28 should be selected such that the engaged NTA fastening system 20 separates prior to substantial elongation of the engaging substrate 26 and/or the receiving substrate 28.

In certain embodiments, the engaging substrate 26 and the receiving substrate 28 may comprise the same web or material. In one such embodiment, the engaging member 22 and the receiving member 24 may represent regions on the material to be fastened.

In embodiments including an engaging substrate 26 and/or a receiving substrate 28, the first NT member 31 may be affixed to the engaging substrate 26 and/or the second NT member 32 may be affixed to the receiving substrate 28 by any bonding means known in the art including, but not limited to, pressure bonds, thermal bonds, adhesive bonds, or ultrasonic bonds. For example, in one embodiment, a hot melt adhesive may be used to affix the first NT member 31 to the engaging substrate 26 and the second NT member 33 to the receiving substrate 28. In some embodiments, the NT member may be formed on the substrate or the substrate may be formed on the NT member. For example, the first NT member 31 may be extruded in a molten or fluid state onto the engaging substrate 26 such that, upon solidification, the first NT member 31 is physically locked into the engaging substrate 26. However, such an example is equally applicable to the other NT members and other substrates.

The first, second, and intermediate NT members 31, 32, 33, may comprise a variety of cohesive and selective adhesive materials. Suitable cohesive and selective adhesive materials include styrenic block copolymers, polyesters, polyamides, polyisoprene, natural and synthetic rubber, olefinic homopolymers, latex, and acrylonitrile copolymers. Oriented variants of the aforementioned list may also serve as suitable NT members. Surface energy modified variants of the aforementioned list may also serve as suitable NT members. In certain embodiments, suitable materials include styrene conjugated diene copolymers (including polystyrene-polybutadiene-polystyrene (SBS) triblock copolymers and polystyrene-polyisoprene-polystyrene (SIS) triblock copolymers), poly(ethylene terephthalate) (PET) and surface energy modified variants, oriented polyamides and surface energy modified variants, and polyolefins (including polypropylene and polyethylene) and surface energy modified variants. Surface energy modification may occur by chemical or high-energy treatments. Suitable surface high-energy modification techniques include but are not limited to corona discharge treatment, plasma treatment, UV radiation treatment, ion beam treatment, electron beam treatment, and certain laser treatments including pulsed lasers. Suitable chemical surface energy modification techniques include, but are not limited to, the use of hydrophobic surface treatments and hydrophilic surface treatments. Other suitable NT members include webs of materials which are both elastic and provide cohesive properties as described in U.S. Pat. No. 6,156,424. In certain embodiments, suitable NT members combinations include SBS or SIS block copolymers/PET, SBS or SIS block copolymers/oriented polyamides, SBS or SIS block copolymers/surface modified oriented polyamides, SBS or SIS block copolymers/polyolefins, SBS or SIS block copolymers/oriented polyolefins, SBS or SIS block copolymers/surface modified polyolefins, and SBS or SIS block copolymers/SBS or SIS block copolymers.

In certain embodiments, the first, second, and intermediate NT member 31, 32, 33, may be in the form of a film, composite, or laminate.

In certain embodiments, the first, second, and intermediate NT members 31, 32, 33 may be selected based upon the T-peel force exhibited by the materials. The T-peel force is calculated by the T-peel test provided below. The T-peel test quantifies the strength of the bond between two materials after a specified time of engagement. While not being bound to theory, when in the fastened configuration (such as shown in FIG. 1B), the intermediate NT member 33 should exhibit greater bond strength with the first NT member 31 than with the second NT member 32. Specifically, it is believed the T-peel force between the first NT member 31 and the intermediate NT member 33 must be greater than the T-peel force between the second NT member 32 and the intermediate NT member 33. In certain embodiments, the T-peel force between the first NT member 31 and the intermediate NT member 33 must be at least about 5% greater than the T-peel force between the second NT member 32 and the intermediate NT member 33. Given the T-peel force data for selected materials provided in Table 1, several suitable materials may be used as the first, second, and intermediate NT members 31, 32, 33.

A suitable cohesive NTA fastening system 20 may comprise a SIS triblock copolymer such as Vector® 4211 (available from Dexco Polymers, Houston, Tex.) as the first NT member 31, Vector® 4211 as the intermediate NT member 33, and a bi-axially oriented polyamide such as Emblem™ 1500 (available from CFP Flexible Packaging, S.p.A., Italy) as the second NT member 32 (the surface of the Emblem™ 1500 material having the lower surface energy is oriented as the regenerative surface 40). As can be appreciated form Table 1, two sheets of Vector® 4211 will lock-up after 6 hours of dwell time whereas Vector® 4211 and Emblem™ 1500 do not lock-up even after 1 week of dwell time. Another suitable cohesive NTA fastening system 20 may again comprise Vector® 4211 as the first NT member 31 and intermediate NT member 33 and a corona treated, bi-axially oriented PET such as Hostaphan® RNK-C (available from Mitsubushi Polymer Film, Gmbh., Wiesbaden, Germany) as the second NT member 32.

A suitable selective adhesive NTA fastening system 20 exhibiting requisite bond strengths may comprise a biaxially-oriented polypropylene film double coated with acrylic such as MW 647 OPPalyte™ (available from ExxonMobil Inc., Luxembourg) as the first NT member 31, Vector® 4211 as the intermediate NT member 33, and a bi-axially oriented polyamide such as Emblem™ 1500 (available from CFP Flexible Packaging, S.p.A., Italy) as the second NT member 32 (the surface of the Emblem™ 1500 material having the lower surface energy is oriented as the regenerative surface 40). Another suitable selective adhesive NTA fastening system 20 may comprise MW 647 OPPalyte™ as the first NT member 31, a SBS triblock copolymer such as Kraton® D1102 (available from Kraton Polymers, Houston, Tex.) as the intermediate NT member 33, and Emblem™ 1500 (either the high or low energy surface) as the second NT member 32. Further information about each of these materials is provided below.

In certain other embodiments, the first, second, and intermediate NT members 31, 32, 33 may be selected based upon the T-peel force exhibited by the materials during the normal life span of the NTA fastening system 20 from manufacture to disposal. Reference is again made to FIGS. 1A-B. FIG. 1A depicts a typical first configuration for the NTA fastening system 20 after manufacturing. The engaging member 22 is not directly engaged with the receiving member 24; however, the intermediate NT member 33 and the second NT member 32 are joined in a face-to-face relationship. The intermediate NT member 33 and the second NT member 32 may be joined for an extended period of dwell time. This period of time may extend several hours, days, or weeks. For example, if the NTA fastening system 20 is incorporated into a disposable absorbent article, it is believed the NTA fastening system 20 may remain in the first configuration (such as shown in FIG. 1A) for several weeks as the absorbent article is transported and stored prior to use. Upon use of the disposable absorbent article, the NTA fastening system 20 may be placed in a fastened configuration (such as shown in FIG. 1B). The NTA fastening system 20 may remain in the engaged configuration until the wearer or caregiver wishes to remove the article. For example, the NTA fastening system 20 may be separated to allow inspection of the article for soiling or for readjustment of the article. It is believed that, when used in most consumer goods, the NTA fastening system 20 will remain in an engaged configuration (see FIG. 1B) for a far shorter period of time than in an initially separated configuration (see FIG. 1A). In the case of absorbent articles, a typical wear time may be in the order of several minutes (e.g., frequent soiling commonly experienced with newborns) to several hours (e.g., overnight wear of approximately 12 hours or more). As a result of these usage patterns, it may be desirable, in certain embodiments, for the first, second, and intermediate NT members 31, 32, 33 to comprise materials exhibiting requisite T-peel forces during the expected use pattern of the NTA fastening system 20 from manufacture to disposal.

In one set of embodiments, the T-peel force of the first NT member 31 and the intermediate NT member 33 after 6 hours of dwell time should be greater than the T-peel force of the second NT member 32 and the intermediate NT 33 material after 1 week of engagement. In other words, the first and intermediate NT members 31, 33 must adhere to one another after a short period of interaction with greater strength than exhibited by the second and intermediate NT members 32, 33 which have had a far longer period of interaction. Otherwise, the intermediate NT member 33 would not separate from the second NTA material 32 which would then prevent exposure of the secondary surface 38 of the intermediate NTA member 33 and exposure of the regenerative surface 40 of the second NT member 32. In certain embodiments, the T-peel force of the first NT member 31 and the intermediate NT member 33 after 6 hours of dwell time should be at least about 5% greater than the T-peel force of the second NT member 32 and the intermediate NT member 33 after 1 week of dwell time. A suitable NTA fastening system 20 exhibiting the aforementioned T-peel force may comprise a SIS triblock copolymer such as Vector® 4211 (available from Dexco Polymers, Houston, Tex.) as the first NT member 31, Vector® 4211 as the intermediate NT member 33, and a bi-axially oriented polyamide such as Emblem™ 1500 (available from CFP Flexible Packaging, S.p.A., Italy) as the second NT member 32 (the surface of the Emblem™ 1500 material having the lower surface energy is oriented as the regenerative surface 40).

Figure 3A:
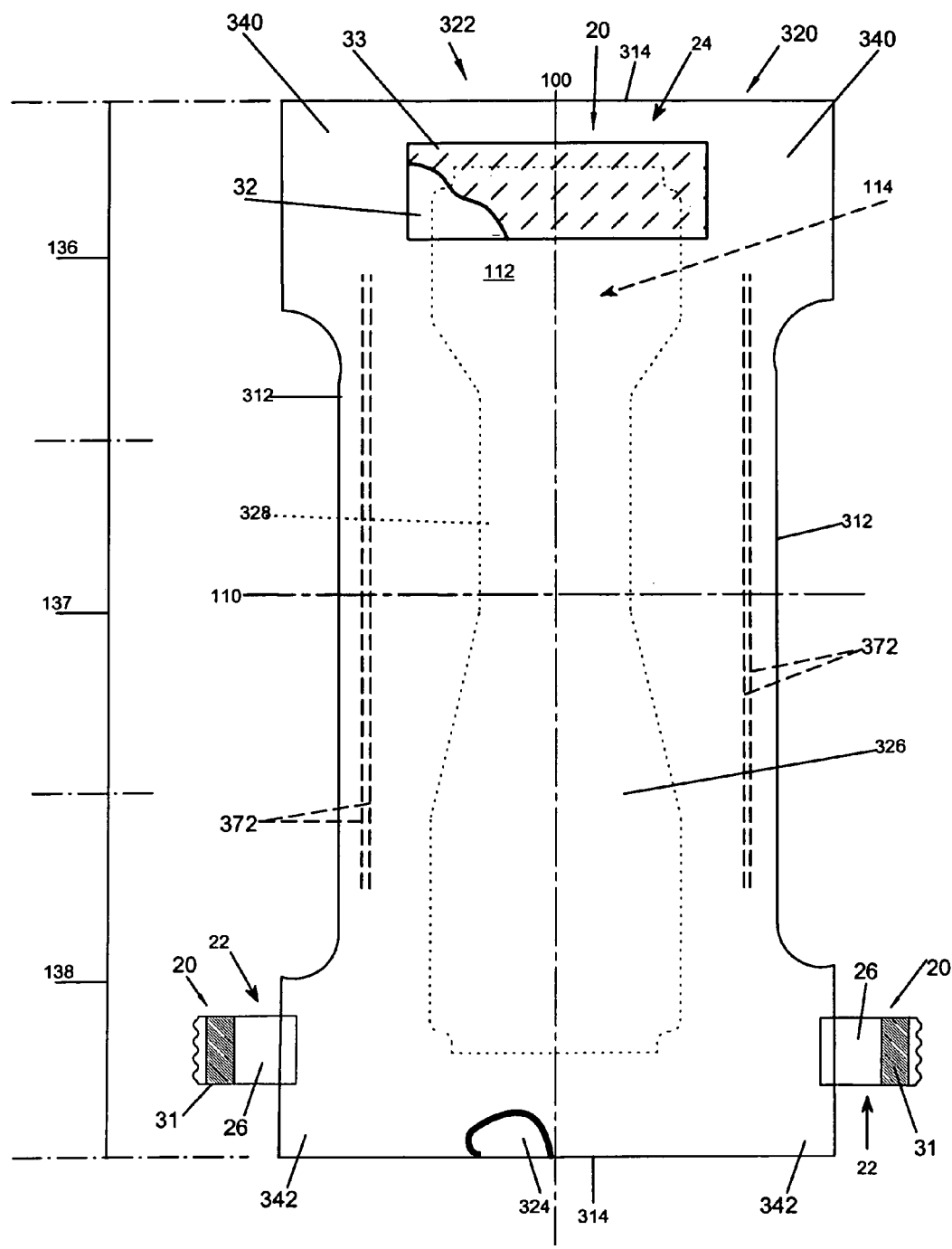
FIGS. 3A-B illustrate exemplary, non-limiting embodiments of an absorbent article in the form of a diaper comprising a non-tacky adhesive fastening system having a regenerative surface.
Figure 3B:
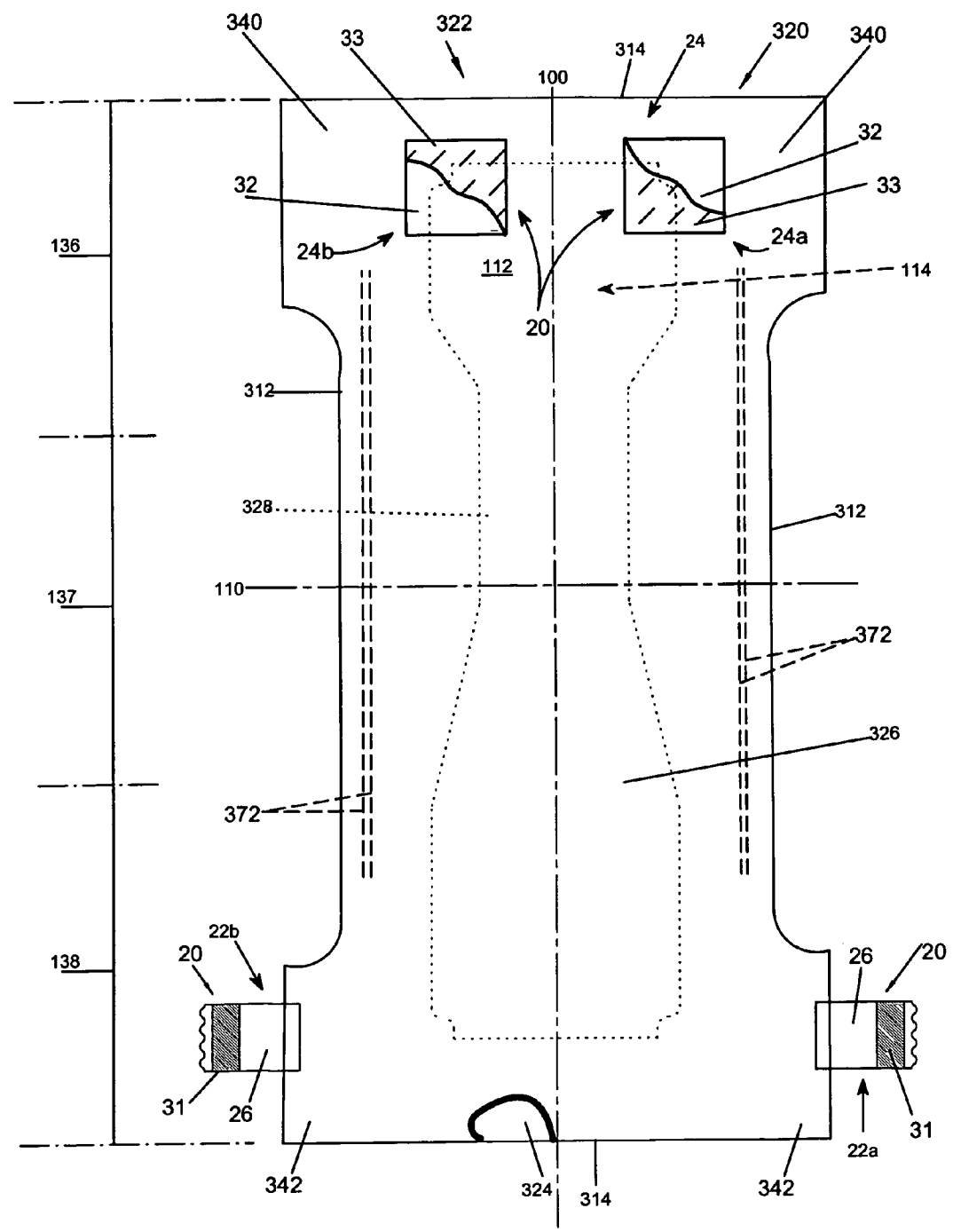

A NTA fastening system may be a component of consumer goods such as absorbent articles and disposable absorbent article. FIGS. 3A-B are plan views of exemplary, non-limiting embodiments of a disposable absorbent article of the present invention in the form of a diaper 320. The diaper 320 is shown in a flat, uncontracted state (i.e., without elastic induced contraction). The body-facing surface 112 of the diaper 320 is facing the viewer and the garment-facing surface 114 is away from the viewer. The diaper 320 includes a longitudinal centerline 100 and a lateral centerline 110. The diaper 320 may comprise a chassis 322. The diaper 320 and chassis 322 are shown to have a front waist region 136, a rear waist region 138 opposed to the front waist region 136, and a crotch region 137 located between the front waist region 136 and the rear waist region 138. The outer periphery of chassis 322 is defined by longitudinal side edges 312 and lateral end edges 314 (which may be referred to as the waist edge). The chassis 322 may have opposing longitudinal side edges 312 that are oriented generally parallel to the longitudinal centerline 100. However, for better fit, longitudinal side edges 312 may be curved or angled to produce, for example, an "hourglass" shape diaper when viewed in a plan view. The chassis 322 may have opposing end edges 314 that are oriented generally parallel to the lateral centerline 110; however the end edges 314 may be curved or angled to provide a more contoured diaper 320.

The chassis 322 is the main body of the diaper 320. Other structures may be added to the chassis 322 to improve the fit and/or functionality of the resulting diaper 320. The chassis 322 comprises at least a liquid permeable topsheet 324, a backsheet 326, and an absorbent core 328 between the topsheet 324 and the backsheet 326. The topsheet 324 may be joined to the core 328 and/or the backsheet 326. The backsheet 326 may be joined to the core 328 and/or the topsheet 324. It should be recognized that other structures, elements, or substrates may be positioned between and the topsheet 324, core 328, and/or backsheet 326. While the topsheet 324, the backsheet 326, and the absorbent core 328 may be assembled in a variety of well-known configurations, preferred diaper configurations are described generally in U.S. Pat. Nos. 3,860,003; 5,151,092; 5,221,274; 5,554,145; 5,569,234; 5,580,411; and 6,004,306.

The topsheet 324 is generally a portion of the diaper 320 that may be positioned at least in partial contact or close proximity to a wearer. Suitable topsheets 324 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 324 is generally supple, soft feeling, and non-irritating to a wearer's skin. In certain embodiments, at least a portion of the topsheet 324 is liquid pervious, permitting liquid to readily penetrate through the thickness of the topsheet 324. A particularly preferred topsheet 324 is available from BBA Fiberweb, Brentwood, Tenn. as supplier code 055SLPV09U.

Any portion of the topsheet 324 may be coated with a lotion (as described in U.S. Pat. Nos. 5,607,760; 5,609,587; 5,635,191; and 5,643,588) and/or may be fully or partially elasticized or may be foreshortened so as to provide a void space between the topsheet 324 and the core 28 (as described in more detail in U.S. Pat. Nos. 4,892,536; 4,990,147; 5,037,416; and 5,269,775).

The core 328 may have opposing longitudinal edges that are oriented generally parallel to the longitudinal centerline 100. However, the core longitudinal edges may be curved or angled to produce, for example as shown in FIGS. 3A-B, an "hourglass" shape when viewed in a plan view. The absorbent core 328 may comprise a wide variety of liquid-absorbent materials commonly used in disposable diapers and other absorbent articles. Examples of suitable absorbent materials include comminuted wood pulp (e.g., air felt creped cellulose wadding); melt blown polymers including co-form; chemically stiffened, modified or cross-linked cellulosic fibers; wraps and tissue laminates; absorbent foams; absorbent sponges; superabsorbent polymers; absorbent gelling materials; or any other known absorbent material or combinations of materials. The absorbent core 328 may comprise a fluid acquisition component which acquires fluid exudates and partitions the exudates away from a wearer's body, a fluid distribution component which distributes/redistributes fluid exudates points away from the point of initial exudate loading, and/or a fluid storage component which retains a majority of the fluid exudates on a weight basis. A suitable absorbent core 328 comprising an acquisition layer, a distribution layer, and/or a storage layer is described in U.S. Pat. No. 6,013,589.

Another suitable absorbent core construction is described in U.S. Publication No. 2004/0167486 to Busam et al. The absorbent core of the aforementioned publication uses no or minimal amounts of absorbent fibrous material within the core. Generally, the absorbent core may include no more than about 20% weight percent of absorbent fibrous material (i.e., [weight of fibrous material/total weight of the absorbent core]×100).

In certain embodiments, the absorbent core 328 may also include layers to stabilize the core components. Such layers include a core cover and a core forming layer. A suitable material for such layers is a spunbonded/meltblown/spunbonded nonwoven having a basis weight between about 10 and 15 g/m² (the meltblown layer comprises <5 g/m²) available from Avgol America, Inc. of Knoxville, N.C. Exemplary absorbent structures for use as the absorbent core 328 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222 and in U.S. Publication Nos. 2004/0162536.

In certain embodiments, the absorbent core 328 may comprise a core wrap. The core wrap at least partially covers the liquid absorbent material of the absorbent core 328. Typically, the core wrap is disposed on a body-facing surface of the absorbent core 328. The core wrap may be useful in immobilizing the liquid absorbent material of the absorbent core 328. The core wrap may comprise a liquid pervious substrate such as a tissue or nonwoven web.

The diaper 320 may comprise other optional structures such as a forming layer adjacent to and, typically, underlying the absorbent core 328. The forming layer is typically disposed between the absorbent core 328 and the backsheet 326. The forming layer provides a substrate on which to deposit the liquid absorbent material during manufacture of the absorbent core 328. In certain embodiments, the forming layer is an air permeable nonwoven web such as described in U.S. Pat. No. 4,888,231.

The backsheet 326 is generally positioned such that it may comprise a portion of the garment-facing surface of the diaper 320. The backsheet 326 may be designed to prevent the exudates absorbed by and contained within the diaper 320 from soiling articles that may contact the diaper 320, such as bed sheets and undergarments. In certain embodiments, the backsheet 326 is substantially urine-impermeable (e.g., liquid water cannot pass through the thickness of the backsheet in the absence of a forcing pressure). Suitable backsheet 326 materials include films such as those manufactured by Tredegar Industries Inc. of Terre Haute, Ind. and sold under the trade names X15306, X10962, and X10964. Other suitable backsheet 326 materials may include breathable materials that permit vapors to escape from the diaper 320 while still preventing exudates from passing through the backsheet 326. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 326 including, but not limited to, surface treatments, particular film selections and processing, particular filament selections and processing, etc.

In certain embodiments, the backsheet 326 may also consist of more than one layer. For example, the backsheet 326 may comprise an outer cover and an inner layer or may comprise two outer covers with an inner layer disposed therebetween. The outer cover may comprise a material having a soft, cloth-like feel such as a soft, non-woven material. The inner layer may comprise a material having suitable barrier characteristics to prevent leakage from the diaper 320. The inner layer may comprise a substantially water-impermeable film or any other suitable backsheet material as presented above. The outer cover and an inner layer may be joined together by adhesive or any other suitable material or bonding technique. A suitable outer cover is available from Corovin GmbH, Peine, Germany as supplier code A18AH0 and a suitable inner layer is available from RKW Gronau GmbH, Gronau, Germany as supplier code PGBR4WPR.

The diaper 320 may comprise one or more leg elastic members 372. The leg elastic members 372 are generally disposed adjacent the longitudinal side edges 312 of the diaper 320. The leg elastic members 372 tend to gather and hold the diaper 320 against the legs of the wearer. The leg elastic members 372 may serve a gasketing function preventing body exudates from leaking out of the diaper 320. The leg elastic members 372 may be joined to or between any of the substrates within the diaper 320 such as the topsheet 324 or backsheet 326. The portion of the diaper gathered by the leg elastic member 372 may be known as an outer leg cuff, a leg gasket, or an elastic cuff. Suitable gasketing cuff construction is further described in U.S. Pat. No. 3,860,003.

The diaper 320 may further comprise waist elastic members (not shown) that are generally disposed adjacent the lateral end edges 314 of the diaper 320 in the front waist region 136 and/or the rear waist region 138. Waist elastic members generally will allow for lateral elongation and recovery. Waist elastic members may be joined to or between any of the substrates within the diaper 320 such as the topsheet 324 or backsheet 326. The waist elastic member may improve the fit and containment of the diaper 320. Other suitable configurations of the elastic waist feature are described in U.S. Pat. Nos. 4,515,595; 4,710,189; 5,151,092; and 5,221,274.

The diaper 320 may include front ears 340 and back ears 342. In certain embodiments, the front and/or back ears 340, 342 may be unitary elements of the diaper 320 (i.e., the ears are not separately manipulative elements secured to the diaper 320, but rather are formed from and are extensions of one or more of the various layers of the chassis 322; such ears are may be referred to as "side-notch ears"). The diaper 320 in FIGS. 3A-B include unitary front and back ears 340, 342. In certain embodiments, the front and/or back ears may be discrete elements that are joined to the chassis 322. Discrete front and/or back ears may be joined to the chassis 322 by any bonding method known in the art. Discrete ears may comprise a layer, element, or substrate that extends from the chassis 322. The front and back ears may be extensible, inextensible, elastic, or inelastic. The front and back ears may be formed from any nonwoven webs, woven webs, knitted fabrics, polymeric and elastomeric films, apertured films, sponges, foams, scrims, and combinations and laminates thereof. In certain embodiments the front and back ears may be formed of a nonwoven/elastomeric material laminate or a nonwoven/elastomeric material/nonwoven laminate. A suitable elastic ear may be formed form a laminate comprising an elastomeric film (such as supplier code X25007 from Tredegar Corp, Richmond, Va.,) disposed between two nonwoven layers (such as supplier code FPN332 from BBA Fiberweb, Brentwood, Tenn.).

The diaper 320 may include a NTA fastening system 20 as presented above. When fastened, the NTA fastening system 20 interconnects the front waist region 136 and the rear waist region 138. When fastened, the diaper 320 contains a circumscribing waist opening and two circumscribing leg openings. As previously presented, the NTA fastening system 20 may comprise an engaging member 22, a receiving member 24, and an intermediate NT material 33. The engaging member 22 may extend laterally from the front waist region 136 or rear waist region 138 of diaper 320. The engaging member 22 may extend laterally from an ear such as the back ear 342 as shown in FIGS. 3A-B. The engaging member 22 may extend from the longitudinal side edge 312 of the diaper 320. In the embodiment depicted in FIGS. 3A-B, the engaging member 22 comprises an engaging substrate 26 with a first NT member 31 disposed thereon.

The receiving member 24 is generally disposed in the waist region opposite the engaging member 22. In FIGS. 3A-B, the receiving member 24 is disposed in the front waist region 136. The receiving member 24 may comprise a receiving substrate 28. The receiving substrate 28 may be a discrete member attached to the diaper 320 or may be a portion of an existing substrate of the diaper 320 with which the receiving member 24 is formed. In FIGS. 3A-B, the receiving substrate 28 may comprise the backsheet 326. The receiving member 24 further comprises a second NT member 32 disposed thereon. FIG. 3A depicts a single receiving member 24 to be used by both engaging members 22. However, the receiving member may be segmented such as shown in FIG. 3B to provide receiving members 24a, 24b. Receiving members 24a, 24b may be engaged by engaging members 22a, 22b, respectively. In the first configuration (as shown in FIGS. 3A-B), the intermediate NT member 33 may be disposed on the second NT member 32. In the first configuration, the intermediate NT member 33 is remote from the first NT member 31.

While in the first configuration, the NTA fastening system 20 allows the diaper 320 to be supplied to the end user with system 20 unfastened. The diaper 320 may be secured for wear by engaging the NTA fastening system 20 which involves engaging the first NT member 31 of the engaging member 22 with the second NT member 32 of the receiving member 24. The diaper 320 may be opened by separating the engaging member 22 from the receiving member 24. In the second configuration, as may be appreciated from FIG. 1C, the secondary surface 38 of the intermediate NT member 33 is exposed and the regenerative surface 40 of the second NT member 32 is exposed. The secondary surface 38 of the intermediate NT member 33 and the regenerative surface 40 the second NT member 32 may be used for subsequent fastening.

In certain embodiments not illustrated, the first configuration of the NTA fastening system 20 may include a release film positioned to cover the exposed surface of the first NT member 31 (i.e., the engaging surface 34 as shown in FIG. 1A) and the intermediate NT member 33 (i.e., the primary surface 36 as shown in FIG. 1A). The release film may serve protect the exposed surfaces during packaging, transport, and storage of the diaper 320. Release films are commercially available and known in the art.

Figure 4A:
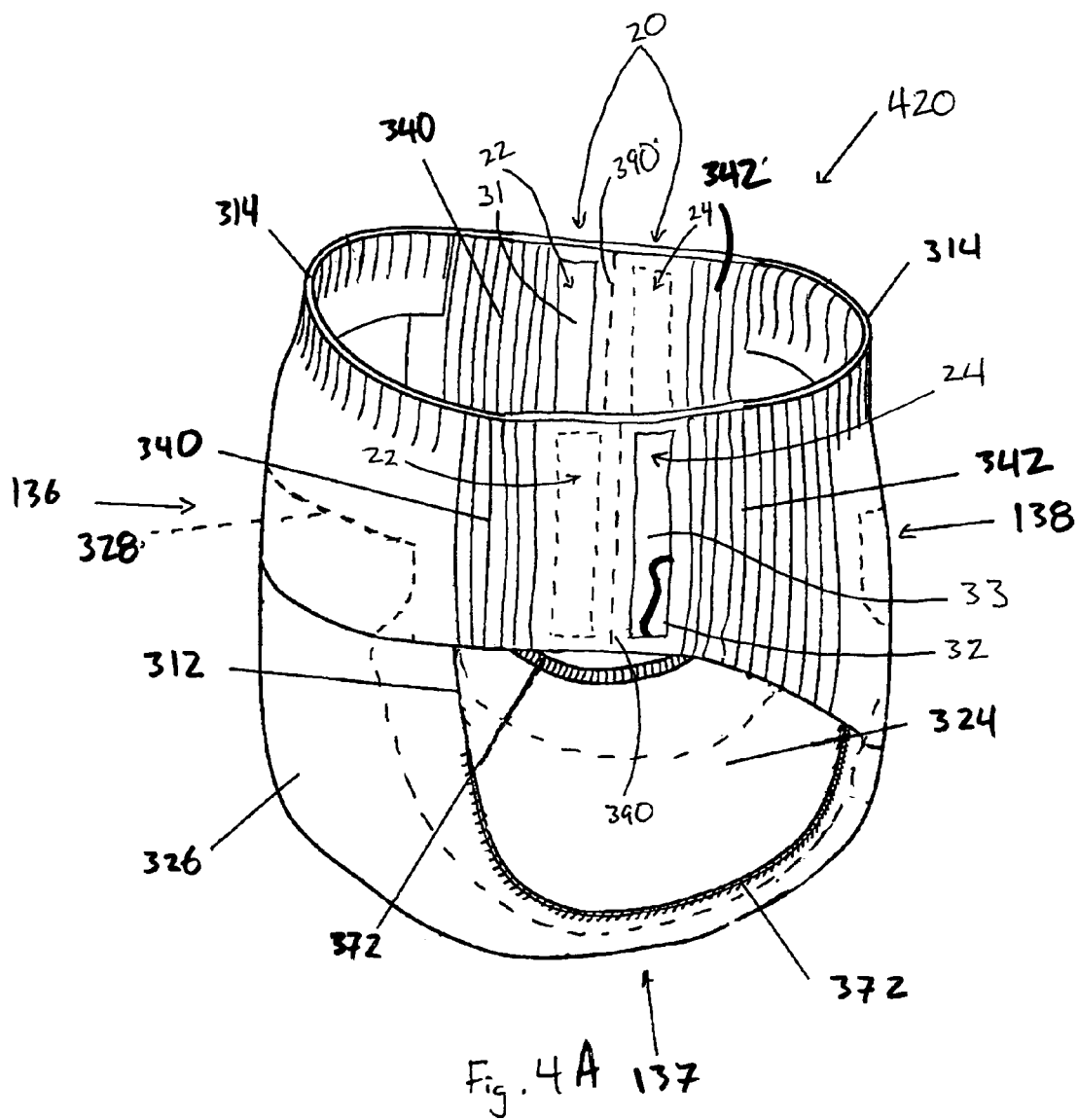
FIGS. 4A-B illustrate an exemplary, non-limiting embodiment of an absorbent article in the form of a pant comprising a non-tacky adhesive fastening system having a regenerative surface.
Figure 4B:
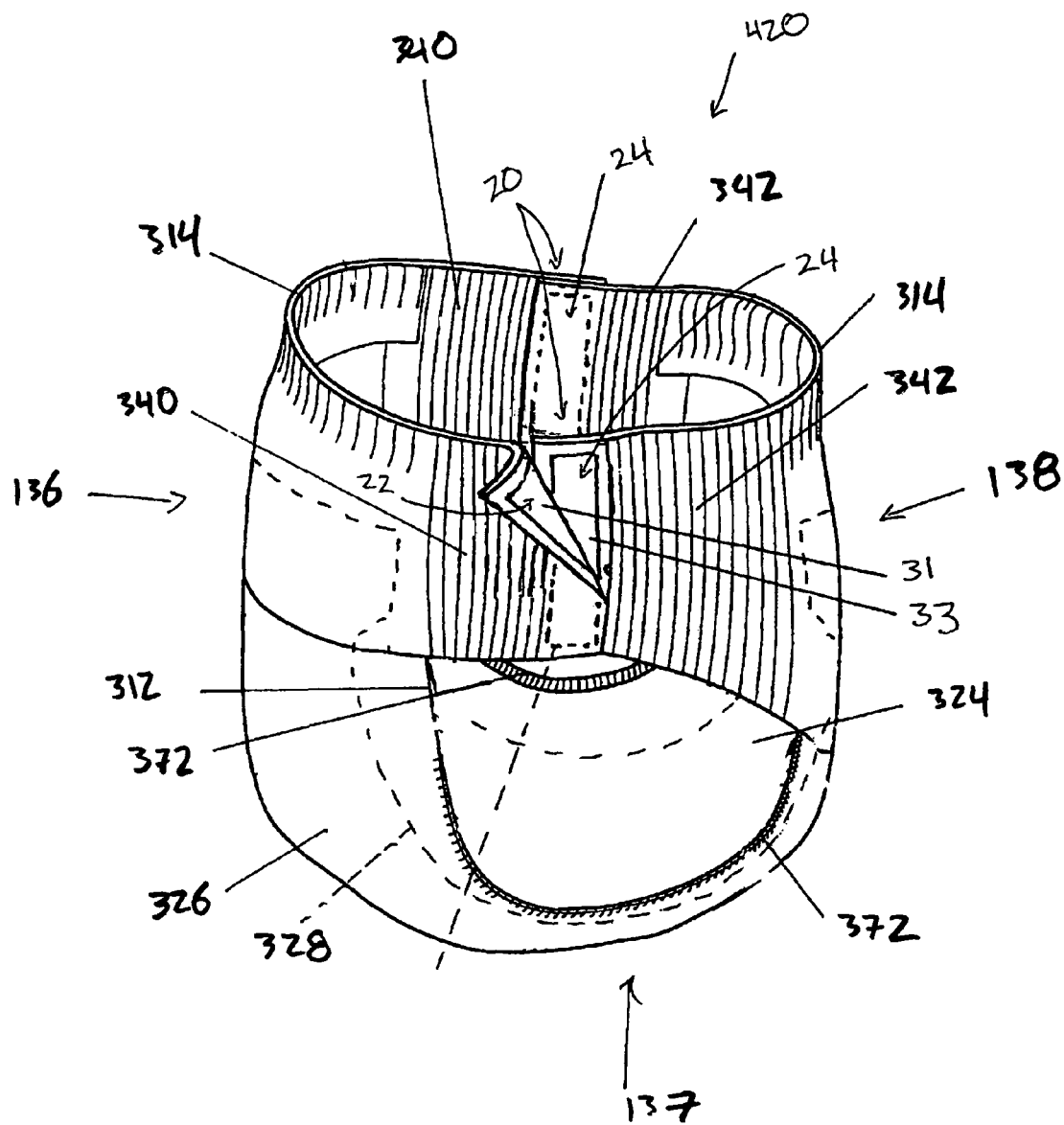

In alternative embodiments, the absorbent article may be pre-formed by the manufacturer to create a pant, which is an absorbent article having a pre-formed waist opening and leg openings. A pant may be preformed by any suitable technique. For example, a pant may be provided by taking the diaper 320 shown in FIGS. 3A-B and engaging the NTA fastening system 20 during manufacture. In another embodiment as shown in FIGS. 4A-B, a pant may be constructed having front ears 340 and back ears 342 joined by a frangible interface 390. (Like reference numerals between FIGS. 4A-B and FIGS. 3A-B identify like elements that may be present in the pant 420). The frangible interface 390 may have a variety of feasible constructions. For instance, the frangible interface 390 may formed by bonding an overlapping portion of the front ear 340 with a portion of the back ear 342. Suitable bonding means are well known in the art and include adhesive bonding, heat bonding, pressure bonding, ultrasonic bonding, and the like. In other embodiments, the front ear 340 and back ear 342 may comprise a continuous member (i.e., the front ear 340 and back ear 342 are formed from a unitary, unseamed structure). In such an embodiment, the frangible interface 390 may be any suitable structure that promotes or facilitates separation of the front ear 340 from the back ear 342. For example, the frangible interface 390 may be a line of weakness such as perforations that will promote or facilitate separation.

The pant 420 may comprise an NTA fastening system 20 similar to the one presented above with regard to FIGS. 3A-B. The NTA fastening system 20 may comprise an engaging member 22, a receiving member 24, and an intermediate NT member 33. As shown in FIGS. 4A-B, the engaging member 22 may be disposed on the front ear 340 and the receiving member 24 may be disposed on the back ear 342; however, this orientation may be reversed. The engaging member 22 comprises an engaging substrate with a first NT member 31 disposed thereon. In this embodiment, the engaging substrate is the substrate that forms the front ear 340. Disposed on to the front ear 340 is the first NT member 31. The receiving member comprises a receiving substrate, which, in this embodiment, is the substrate that forms the back ear 342. Disposed on the back ear 342 is a second NT member 32. In the first configuration (as shown in FIG. 4A), the intermediate NT member 33 may be disposed on the second NT member 32. In the first configuration, the intermediate NT member 33 is remote from the first NT member 31.

The pant 420 may be donned by a wearer in the configuration shown in FIG. 4A. At some point after donning, the frangible interface 390 may be broken thereby separating the front ear 340 from the back ear 342. The frangible interface 390 may be broken to allow inspection of the pant 420 for soiling or readjustment of the article for better fit. The pant 420 may be reattached by engaging the first NT member 31 with the intermediate NT member 33, such as is shown in FIG. 4B. When engaged, the NTA fastening system 20 interconnects the front waist region 36 and the rear waist region 38. When fastened, the pant 20 exhibits a circumscribing waist opening and two circumscribing leg openings. After a period of wear, the pant 420 may be opened by separating the engaging member 22 from the receiving member 24. In this second configuration, as may be appreciated from FIG. 1C, the secondary surface 38 of the intermediate NT member 33 is exposed and the regenerative surface 40 of the second NT member 32 is exposed. The secondary surface 38 of the intermediate NT member 33 and the regenerative surface 40 the second NT member 32 may be used for subsequent fastening.

Figure 5:
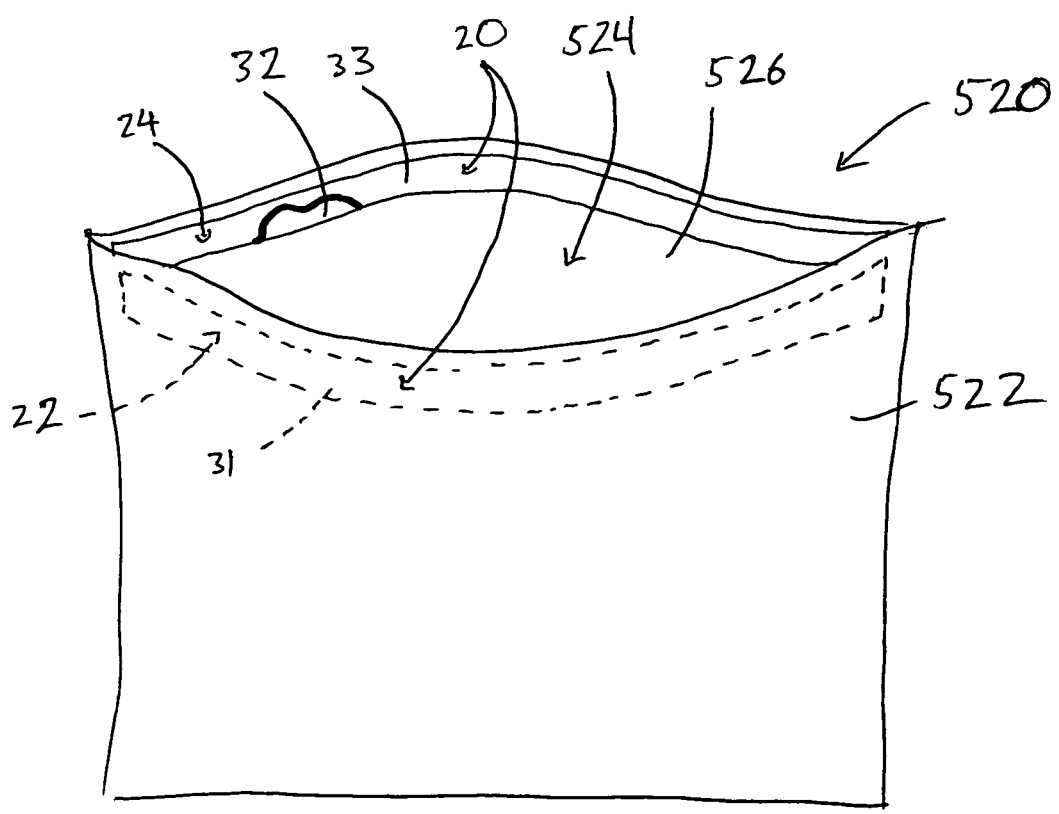
FIG. 5 illustrates a suitable embodiment of a reclosable bag comprising a non-tacky adhesive fastening system having a regenerative surface.

Other consumer goods incorporating an NTA fastening system 20 include reclosable bags or containers. For example, FIG. 5 depicts a suitable embodiment of a reclosable bag 520 comprising an NTA fastening system 20. The reclosable bag 520 may comprise an overwrap 522 that is configured to form an internal void 524. The overwrap 522 may comprise a variety of materials including, but not limited to, polymeric films, nonwovens, wovens, foils, fabrics, papers, cardboard, elastic sheets, and combinations thereof. The reclosable bag 520 may be sized such that the internal void 524 is capable of receiving a stored item (i.e., any item which a manufacturer or end user wishes to place in the bag). The internal void 524 may be accessed through a reclosable aperture 526.

The NTA fastening system 20 comprises an engaging member 22, a receiving member 24, and an intermediate NT member 33. The engaging member 22 comprises an engaging substrate with a first NT member disposed thereon. In the embodiment shown in FIG. 5, the engaging substrate is the overwrap 522. Disposed on to overwrap 522 is the first NT member 31. The receiving member comprises a receiving substrate, which, in the embodiment shown in FIG. 5, is the overwrap 522. Disposed on the overwrap 522 is a second NT member 32. In the first configuration (as shown in FIG. 5), the intermediate NT member 33 may be disposed on the second NT member 32. In the first configuration, the intermediate NT member 33 is remote from the first NT member 31.

The reclosable bag 520 may be closed by engaging the first NT member 31 of the engaging member 22 with the intermediate member 33. The reclosable bag 520 may be opened by separating the engaging member 22 from the receiving member 24. In the second configuration, as may be appreciated from FIG. 1C, the secondary surface 38 of the intermediate NT member 33 is exposed and the regenerative surface 40 of the second NT member 32 is exposed; the secondary surface 38 of the intermediate NT member 33 and the regenerative surface 40 the second NT member 32 may be used for subsequent fastening and closure of the reclosable bag 520.

Test Methods

For each of the sample preparations described below, the materials must be handled with care to avoid contact with hands, skin, or other contaminating surfaces. Clean sheets of untreated paper may be used to protect the surfaces of the test material during the sample preparation.

T-Peel Test

This method is used to determine the T-Peel force/strength of the bond between two materials after a predetermined time of engagement.

Sample Preparation—

The sample preparation for T-peel test will vary based on whether the material is available as a discrete web or is incorporated in a product.

Figure 6A:
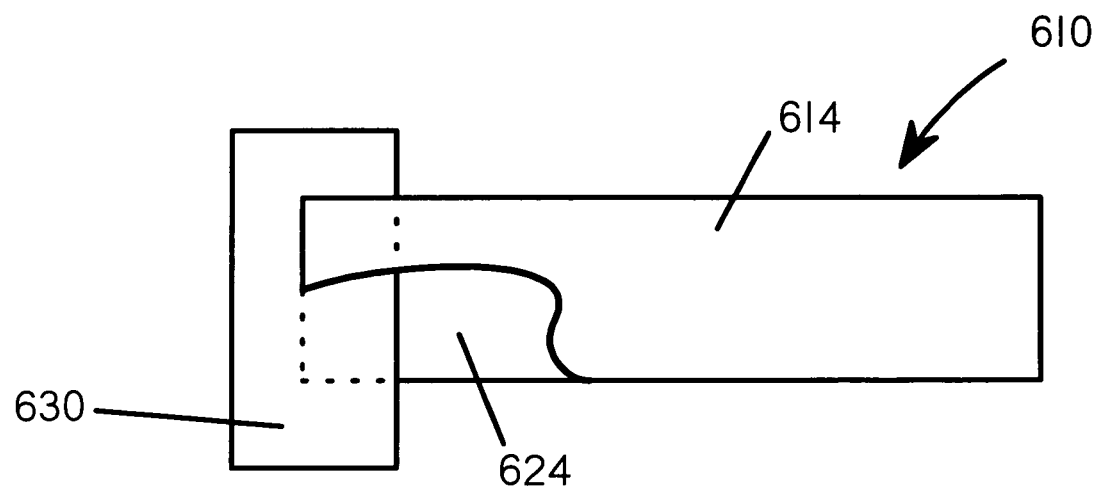
FIG. 6A illustrates a suitable sample preparation for the T-Peel Test.
Figure 6B:
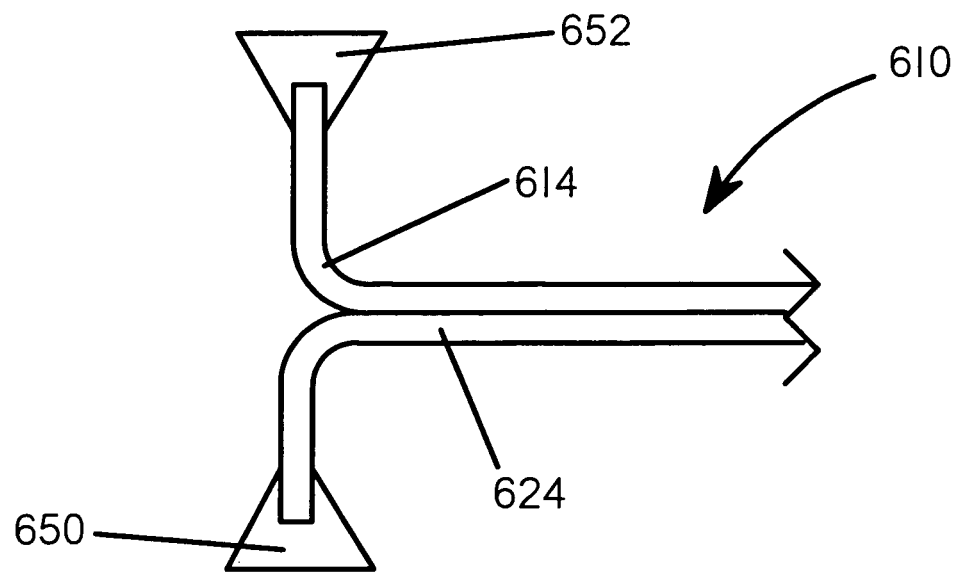
FIG. 6B illustrate the sample of FIG. 6A positioned in a tensile tester.

FIGS. 6A-B illustrate a bonded sample 610 formed according to the directions provided below.

A first material 614 is resized to the dimensions of about 2.54 cm (1") wide×10.80 cm (4") long. In instances where the first material 614 is elastomeric, the first material 614 is to be backed with like sized piece of poly(ethylene terephthalate) film or paper using double sided tape.

A second material 624 is resized to the dimensions of about 2.54 cm (1") wide×10.80 cm (4") long. In instances where the second material 624 is elastomeric, the second material 624 is backed with like sized piece of poly(ethylene terephthalate) film or paper using double sided tape.

A suitable double sided tape for use in backing either the first material 614 or the second material 624 is available under supplier code FT 239 from Avery Denninson Corp., Painesville, Ohio or under supplier code 9589 from 3M Corp., St. Paul, Minn. Any suitable PET film may be used having a thickness of at least about 2 mil (0.05 mm).

As shown in FIG. 6A, the first material 614 is bonded to the second material 624 to for a bonded sample 610. Bonding is to be performed on a flat, clean, rigid surface such as a countertop. The first material 614 is applied to the second material 624 so as to avoid wrinkles. The first material 614 should be substantially coterminous with the second material 624. It should be recognized that the first material 614 and the second material 624 may be first bonded and then resized to yield a 2.54 cm (1") wide×10.80 cm (4") long bonded sample 610.

A small piece of release paper 630 (such as a double sided silicone coated paper available as supplier code HV100-473/473 from Fox River Associates, LLC., Geneva, Ill.) is placed between the first material 614 and the second material 624 and may span the width of the first material 614 and the second material 624. The release paper 630 should not be inserted more than a few millimeters between the first material 614 and the second material 624 (i.e., no more than 10% of the total bonded length). The bonded sample 610 is rolled with a 4.5 pound (2 kg) HR-100 ASTM 80 shore rubber-faced roller. Two full strokes (i.e., back and forth) are applied to the sample at a speed of approximately 10 mm/sec. The bonded area should be approximately 1" (2.54 cm) wide by 4" long (10.80 cm) minus any area separated by the release paper 630. The bonded sample 610 is subjected to a dwell time of either 6 hours or 7 days at a temperature of 60° C. and a pressure of 0.8 N/cm² prior to testing to provide a T-Peel Force.

A skilled artisan should recognize that bonded specimens of other dimensions may be used in the T-Peel Method. The dimensions of the first material 614 and the second material 624 may vary from those listed above; however, the effective bonding area should be used to normalize the resultant T-Peel force recorded per inch of bonded width (i.e., the bonded width being the width of the bonded area measured substantially parallel to the grip width once the sample is mounted in the tensile tester).

Test Conditions—

The T-Peel test method is performed in a controlled room at 22° C.+/−2° C. and RH 50%+/−10%. Suitable instruments for this test include tensile testers commercially available from Instron Engineering Corp., Canton, Mass. (e.g Instron 5564) or from MTS Systems Corp., Eden Prairie, Minn. (e.g. Alliance RT/1 or Sintech 1/S). The following procedure illustrates the measurement when using the Instron 5564. The instrument is interfaced with a computer loaded with the Instron® Merlin™ Material Testing Software which controls the testing parameters, performs data acquisition and calculation, and provides graphs and data reports. The instrument is configured with a data acquisition speed of 50 Hz. Any resulting graphs are plotted using the Average Value (integral) setting on the instrument. A load cell is selected so that the forces to be measured will be between 10% and 90% of the capacity of the load cell or the load range used (e.g., typically, a 10N to 100N load cell). The instrument is calibrated to an accuracy of at least 1% and, ideally, less than 0.1% according to the manufacturer's instructions.

As shown in partial cross-sectional view of FIG. 6B, the instrument has two grips: a stationary grip 650 and a movable grip 652. The grips 650, 652 used are wider than the sample; typically, 2 inch (5.08 cm) wide grips are used. The grips 650, 652 are air-actuated grips and designed to concentrate the entire gripping force along a plane perpendicular to the direction of testing stress. The distance between the lines of the gripping force (i.e., gauge length) is set to 1" (2.54 cm). The load reading on the instrument is zeroed to account for the mass of the fixture and grips. The bonded sample 610 is mounted into the grips 650, 652 as shown in FIG. 6B. The bonded sample 610 is mounted so that the free edge (i.e., edge separated by the release paper 630) of the first material 614 is in the movable grip 652 and the (i.e., edge separated by the release paper 630) of the second material 624 is in the stationary grip 650. The bonded sample 610 is mounted with a minimal amount of slack in the first material 614 and the second material 624. The load cell is zeroed.

The first material 614 is separated from the second material 624 using a crosshead speed of 12 inches/min (305 mm/min). An average load is calculated as the average load between about 1" (about 25 mm) and about 3.5" (about 88 mm) displacement. For samples 610 that do not meet the dimensions provided in the Sample Preparation, the average load is calculated from the loads acquired from the crosshead extension between about 25% to about 87.5% of the sample length. For example, if the sample is 6 inches long, the average load is calculated between about 1.5 inches and about 5.24 inches of crosshead extension. The average load is normalized to a width of 1" (2.54 cm) as follows: normalized load=average load÷initial bond width in inches. The average load is the T-peel force of the sample.

Probe Tack Test Method

Figure 7:
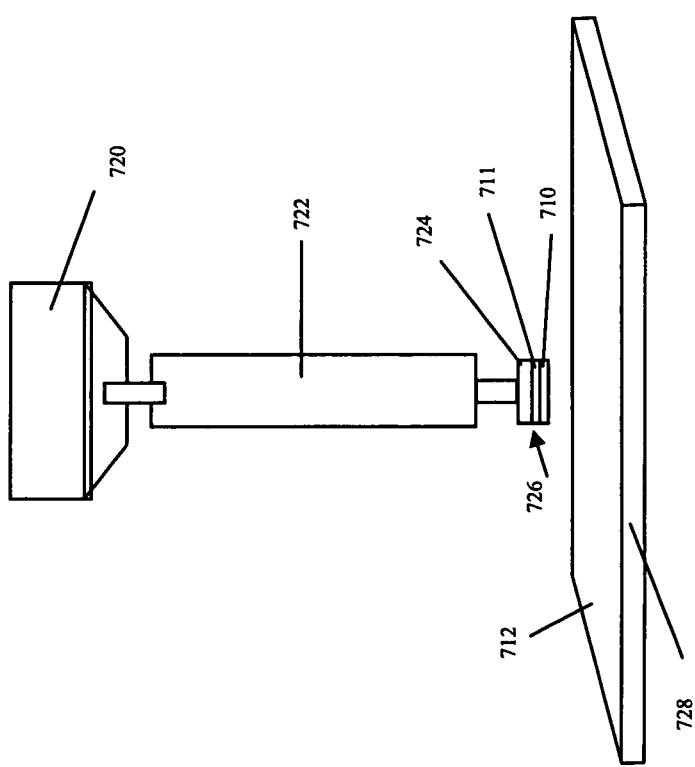
FIG. 7 illustrates a suitable sample and instrument configuration for the Probe Tack Test.

This method is used to determine the tackiness of select materials when placed in contact with a standard surface at a controlled rate and pressure. This test is derived from ASTM D Test Method No. 2979-01 which is directed to Pressure Sensitive Adhesives. FIG. 7 depicts a suitable sample and instrument configuration.

Sample Preparation—

For the Instron 5564 instrument listed above, the sample is prepared as follows. The sample material 710 is bonded to a piece double-sided tape 711 (such as FT 239 available from Avery Denninson Corp., Painesville, Ohio). The sample material 710/double sided tape 711 is resized to 1"×1" (approx. 2.5×2.5 cm). The opposite side of the double sided tape 711 is bonded to the anvil face 726 of a probe anvil 724. The sample material 710/double sided tape 711 is cut with a knife to fit to the anvil face 726. The sample material 710/double sided tape 711 is to be cut without contaminating or touching the surface of the sample material 710 to be tested. The surface area of the sample material 710 is approximately the same as the anvil face 726.

Test Conditions—

The Probe Tack Test is performed in a controlled room at 22° C.+/−2° C. and RH 50%+/−10%. Suitable instruments for this test include tensile testers commercially available from Instron Engineering Corp., Canton, Mass. (e.g. Instron 5564) or equivalent tensile testers.

The instrument is interfaced with a computer which controls the testing parameters, performs data acquisition and calculation, and provides graphs and data reports. The probe anvil 724 is mounted to a probe body 722 which is connected to a load cell 720. The probe anvil 724 is cylindrical is shape and has a substantially circular anvil face 726. The anvil face 726 has a diameter of approximately 1.1 cm and a surface area of 0.95 $cm^2$. The load cell 720 is selected so that the forces to be measured will be between 10% and 90% of the capacity of the load cell 720. The bottom stationary side of the Instron is mounted with a fixed planar plate 728 with a predominate surface parallel to the anvil face 726. The plate 728 is made from a material that will exhibit a negligible degree of deformation or compression during the test (e.g., a steel plate). A standard surface 712 is joined to the plate 728. For purposes of this test method, the standard surface 712 is a synthetic skin available from IMS, Inc., Milford, Conn. as VITROSKINT™ N19. Before testing, the mimic skin is conditioned according to the supplier's instruction. The mimic skin is bonded to the plate 728 to maintain the mimic skin a substantially planar configuration during testing.

Before measurement, the load reading on the instrument is zeroed to account for the mass of the probe. The anvil face 726 along with the sample material 710 are brought into contact with the standard surface 712 at speed of 1 mm/min until a compression load of 95 gram-force (i.e., corresponding to 9.79 kPa, for a probe of 1.1 cm diameter) is achieved. After a 1 second delay while maintaining the 95 grams force, the probe is pulled away from the standard surface at speed of 10 mm/min. The Maximum Load is then recorded as gram-force. The maximum load is normalized per area of the anvil face: normalized Maximum load=measured maximum load÷anvil face surface area.

Low surface adhesion (i.e., non-tacky) is quantified as a measurement of less than 50 grams force (gf) according to the Probe Tack Test Method. In certain embodiments, low surface adhesion may be less than 40 gf; alternately, less than 30 gf; alternately, less than 20 gf; alternately, less than 10 gf; or alternately, less than 5 gf. Kraton® D1102 and Kraton® D1111 available from Kraton Polymers, Houston, Tex., exhibit a probe tack force of about 2 gf. Vector® 4211 available from Dexco Polymers, Houston, Tex., exhibits a probe tack force of about 2 gf. By way of comparison, Kraton® D1107 available from Kraton Polymers, Houston, Tex., exhibits a probe tack force of about 168 gf. Furthermore, a common pressure sensitive adhesive available as AD FT 239 from Avery Denison, Turnhout, Belgium, exhibits a probe tack force of about 129 gf.

Examples

Samples of the materials listed below are tested according to the T-Peel Test Method. The samples are subjected to a dwell time of 6 hours (and, in some cases, for a 1 week) at a temperature of 60° C. and under 0.8 $N/cm^2$ pressure. The T-Peel force is an average from at least 3 samples and is normalized to units of Newtons per inch of initial sample width. Table 1 provides the tested combinations. The materials tested are referenced by the acronyms provided.

D1102: Kraton® D1102 is available from Kraton Polymers, Houston, Tex. D1102 is a styrene/butadiene/styrene triblock elastomer (16% diblock and 28% styrene). D1102 is extruded to form about a 2-5 mil thick film.

D1111: Kraton® D1111 is available from Kraton Polymers, Houston, Tex. D1111 is a styrene/isoprene/styrene triblock elastomer (15% diblock and 22% styrene). D1111 is extruded to form about a 2-5 mil thick film.

4211: Vector® 4211 is available from Dexco Polymers LP, Houston, Tex. 4211 is a styrene/isoprene/styrene triblock elastomer (0% diblock and 20% styrene). 4211 is extruded to form about a 2-5 mil thick film.

PET: PET is a corona treated, bi-axial oriented poly(ethylene terephthalate) available under tradename Hostaphan® RNK-C from Mitsubishi Polyester Film Gmbh, Wiesbaden, Germany. The PET is supplied as a 12 microns thick film.

oPA54: oPA54 is a bi-oriented polyamide film having a supplier reported surface energy of 54 mN/m. The bi-oriented polyamide 54 is 15 microns thick and is available from CFP Flexible Packaging S.p.A., Italy, under the tradename of Emblem™1500.

oPA40: oPA40 is bi-oriented polyamide film having a supplier reported surface energy of 40 mN/m. The bi-oriented polyamide 40 is the untreated side of the oPA54 Emblem™ film. oPA40 is supplied as a film 15 microns thick.

PE50: PE50 is the corona treated side of a polyethylene film manufactured by Nordenia International AG as supplier code KC 2672.770. PE50 has a thickness of 95 microns and a supplier reported surface energy of 50 mN/m. PE50 has a density of 0.93 $g/cm^3$.

PE33: PE33 is the untreated side of the PE50 polyethylene film manufactured by Nordenia International AG. PE33 has a supplier reported surface energy of 33 mN/m.

PP44: PP44 is the corona treated side of a polypropylene film having a supplier reported surface energy of 44 mN/m available as supplier code 14461 from Huhtamaki Forchheim GmbH, Germany. PP44 has a thickness of 70 microns and a density of 0.9 $g/cm^3$.

PP33: PP33 is the untreated side of the PP44 polypropylene film manufactured by Huhtamaki Forchheim GmbH, Germany. PP33 has a surface energy of 33 mN/m.

oPP42: oPP42 is a biaxially-oriented polypropylene film double coated with acrylic and is manufactured by ExxonMobil Inc., Luxembourg under the trade name MW 647 OPPalyte™. oPP42 has a supplier reported surface energy of 42 mN/m and a thickness of 40 microns.

TABLE 1

|      | D1102 | D1111 | 4211 |
|------|-------|-------|------|
| PET  | 6.5 ± 0.2 (6 h) | 2.6 ± 0.5 (6 h) | 8.0 ± 0.1 (6 h) |
|      | 8.0 ± 0.6 (1 w) | 9.0 ± 0.2 (1 w) | 16 ± 4 (1 w) |
| oPA54 | 5.0 ± 0.5 (6 h) | 4.4 ± 1.9 (6 h) | 4.2 ± 0 (6 h) |
|      | 5.8 ± 0.4 (1 w) | 8.0 ± 5.0 (1 w) | Lock Up (1 w) |
| oPA40 | 3.1 ± 0.1 (6 h) | 1.9 ± 1.0 (6 h) | 3.6 ± 0.2 (6 h) |
|      | 5.1 ± 0.3 (1 w) |  | 5.8 ± 1.3 (1 w) |
| PE50 | 11.9 ± 0.3 (6 h) | 3.1 ± 2.4 (6 h) | 6.9 ± 0.6 (6 h) |
|      |  |  | Lock Up (3 d) |
| PE33 | 2.2 ± 0.1 (6 h) | 0.5 ± 0.7 (6 h) | 0.5 ± 0.2 (6 h) |
| PP33 | 8.9 ± 0.1 (6 h) | 3.0 ± 3.0 (6 h) | 7.3 ± 0.7 (6 h) |
| PP44 | 9.0 ± 0.3 (6 h) | 5.4 ± 1.6 (6 h) | 8.5 ± 0.8 (6 h) |
|      |  | 17.0 ± 5.0 (1 w) |  |
| oPP42 | Lock Up (6 h) | 4.4 ± 0.9 (6 h) | Lock Up (6 h) |
| D1111 | — | 4.7 ± 0.5 (6 h) | — |
|      |  | 17.0 ± 1.0 (1 w) |  |
| 4211 | — | — | Lock Up (6 h) |

All values are in N/inch.
6 h = 6 hours of dwell time.
1 w = 1 week of dwell time.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with any definition or meaning of the term in a document incorporated by reference, the definition or meaning assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A non-tacky adhesive fastening system having a first configuration and a second configuration, wherein the non-tacky adhesive fastening system in the first configuration comprises:
   a) an engaging member comprising a first non-tacky member, said first non-tacky member comprises an engaging surface and a fixed surface, and
   b) a receiving member comprising:
      i) an intermediate non-tacky member having a primary surface and a secondary surface, and
      ii) a second non-tacky member having a regenerative surface and a fixed surface,
         wherein the secondary surface of the intermediate non-tacky member is refastenably joined to the regenerative surface of the second non-tacky member and wherein the engaging surface of the first non-tacky member is remote from the primary surface of the intermediate non-tacky member; and
   wherein the non-tacky adhesive fastening system in the second configuration comprises:
      a) the engaging member comprising the first non-tacky member and the intermediate non-tacky member; wherein the primary surface of the intermediate non-tacky member is joined to the engaging surface of the first non-tacky member, and
      b) the receiving member comprises the second non-tacky member;
   wherein the second configuration is formed upon fastening the engaging surface of the first non-tacky member to the primary surface of the intermediate non-tacky member and separating the engaging member from the receiving member.

2. The non-tacky adhesive fastening system of claim 1 further comprising an engaging substrate, wherein the first non-tacky member is disposed on said engaging substrate.

3. The non-tacky adhesive fastening system of claim 2 wherein the engaging substrate exhibits less than about 10% strain when subjected to a minimal T-peel force allowing for separation of the engaging member from the receiving member.

4. The non-tacky adhesive fastening system of claim 1 further comprising a receiving substrate, wherein the second non-tacky member is disposed on said receiving substrate.

5. The non-tacky adhesive fastening system of claim 4 wherein the receiving substrate exhibits less than about 10% strain when subjected to a minimal T-peel force allowing for separation of the engaging member from the receiving member.

6. The non-tacky adhesive fastening system of claim 1 wherein the first non-tacky member, the intermediate non-tacky member, and the second non-tacky member are selected from the group consisting of styrenic block copolymers, poly(ethylene terephthalate), polyamides, polyisoprene, natural and synthetic rubber, polyolefins, oriented variants thereof, and combinations thereof.

7. The non-tacky fastening system of claim 1 wherein the second configuration is formed upon fastening the engaging surface of the first non-tacky member to the primary surface of the intermediate non-tacky member for at least about 2 hours of dwell time prior to separating the engaging member from the receiving member.

8. The non-tacky fastening system of claim 1 wherein the second configuration is formed upon fastening the engaging surface of the first non-tacky member to the primary surface of the intermediate non-tacky member for at least about 6 hours of dwell prior to separating the engaging member from the receiving member.

9. An absorbent article comprising the non-tacky adhesive fastening system of claim 1.

10. A reclosable bag comprising the non-tacky adhesive fastening system of claim 1.

11. A non-tacky adhesive fastening system comprising:
   a) an engaging member comprising a first non-tacky member, said first non-tacky member comprises an engaging surface and a fixed surface, and
   b) a receiving member comprising:
      i) an intermediate non-tacky member having a primary surface and a secondary surface, and
      ii) a second non-tacky member having a regenerative surface and a fixed surface,
         wherein the secondary surface of the intermediate non-tacky member is refastenably joined to the regenerative surface of the second non-tacky member, and
         wherein, upon fastening, the engaging surface of the first non-tacky member and the primary surface of the intermediate non-tacky member exhibit a T-peel force greater than a T-peel force exhibited by the secondary surface of the intermediate non-tacky member and the regenerative surface of the second non-tacky member.

12. The non-tacky fastening system of claim 11 wherein the engaging surface of the first non-tacky member is fastened to the primary surface of the intermediate non-tacky member for at least about 2 hours of dwell time prior to separating the engaging member from the receiving member.

13. The non-tacky adhesive fastening system of claim 11 wherein, upon fastening, the engaging surface of the first non-tacky member and the primary surface of the intermediate non-tacky member exhibit a T-peel force after 6 hours of dwell time greater than a T-peel force exhibited by the secondary surface of the intermediate non-tacky member and the regenerative surface of the second non-tacky member after 6 hours of dwell time.

14. The non-tacky adhesive fastening system of claim 13 wherein, upon fastening, the engaging surface of the first non-tacky member and the primary surface of the intermediate non-tacky member exhibits a T-peel force after 6 hours of dwell time of about 5% greater than a T-peel force exhibited by the secondary surface of the intermediate non-tacky member and the regenerative surface of the second non-tacky member after 6 hours of dwell time.

15. The non-tacky adhesive fastening system of claim 11 wherein, upon fastening, the engaging surface of the first non-tacky member and the primary surface of the intermediate non-tacky member exhibit a T-peel force after 6 hours of dwell time greater than a T-peel force exhibited by the secondary surface of the intermediate non-tacky member and the regenerative surface of the second non-tacky member after 1 week of dwell time.

16. The non-tacky adhesive fastening system of claim 11 wherein the first non-tacky member, the intermediate non-tacky member, and the second non-tacky member are selected from the group consisting of styrenic block copolymers, poly(ethylene terephthalate), polyamides, polyisoprene, natural and synthetic rubber, polyolefins, oriented variants thereof, and combinations thereof.

17. An absorbent article comprising an absorbent assembly having opposing longitudinal edges, a front waist region, a rear waist region and a crotch region between and connecting said front and said rear waist regions; an ear disposed transversely from the longitudinal edge of the absorbent assembly, said ear interconnecting said front waist region and said rear waist region; and a non-tacky adhesive fastening system joining the ear to either the front waist region or rear waist region, wherein said non-tacky adhesive fastening system has a first configuration and a second configuration, and wherein the non-tacky adhesive fastening system comprises:
 a) an intermediate non-tacky member having a primary surface and a secondary surface
 b) an engaging member comprising a first non-tacky member, said first non-tacky member comprises an engaging surface and a fixed surface, and
 c) a receiving member comprising a second non-tacky member, said second non-tacky member having a regenerative surface and a fixed surface;
 wherein in the first configuration of said non-tacky adhesive fastening system, the secondary surface of the intermediate non-tacky member is refastenably joined to the regenerative surface of the second non-tacky member and said primary surface of the intermediate member is remote from the engaging surface of the first non-tacky member;
 wherein in the second configuration of said non-tacky adhesive fastening system, the primary surface of the intermediate non-tacky member is joined to the engaging surface of the first non-tacky member and the secondary surface of the intermediate member is remote from the regenerative surface of the second non-tacky member, and
 wherein the second configuration is formed upon fastening the engaging surface of the first non-tacky member to the primary surface of the intermediate non-tacky member and separating the engaging member from the receiving member.

18. The absorbent article of claim 17 wherein, upon fastening, the engaging surface of the first non-tacky member to the primary surface of the intermediate non-tacky member exhibit a T-peel force greater than a T-peel force exhibited by the secondary surface of the intermediate non-tacky member and the regenerative surface of the second non-tacky member.

19. The absorbent article of claim 17 wherein the engaging surface of the first non-tacky member and the primary surface of the intermediate non-tacky member exhibit a T-peel force after 6 hours of dwell time of about 5% greater than a T-peel force exhibited by the secondary surface of the intermediate non-tacky member and the regenerative surface of the second non-tacky member after 6 hours of dwell time.

20. The absorbent article of claim 17 wherein, upon fastening, the engaging surface of the first non-tacky member to the primary surface of the intermediate non-tacky member exhibit a T-peel force after 6 hours of dwell time greater than a T-peel force exhibited by the secondary surface of the intermediate non-tacky member and the regenerative surface of the second non-tacky member after 1 week of dwell time.

21. The absorbent article of claim 17 wherein the first non-tacky member, the intermediate non-tacky member, and the second non-tacky member are selected from the group consisting of styrenic block copolymers, polyethylene terephthalate), polyamides, polyisoprene, natural and synthetic rubber, polyolefins, oriented variants thereof, and combinations thereof.

22. The absorbent article of claim 17 wherein the second configuration is formed upon fastening the engaging surface of the first non-tacky member to the primary surface of the intermediate non-tacky member for at least about 2 hours of dwell time prior to separating the engaging member from the receiving member.

* * * * *